(12) United States Patent
Masuda et al.

(10) Patent No.: US 10,363,013 B2
(45) Date of Patent: Jul. 30, 2019

(54) ULTRASOUND DIAGNOSIS APPARATUS AND MEDICAL IMAGE DIAGNOSIS APPARATUS

(71) Applicant: Toshiba Medical Systems Corporation, Otawara-shi (JP)

(72) Inventors: Takashi Masuda, Utsunomiya (JP); Shouichi Nakauchi, Nasushiobara (JP); Takashi Koyakumaru, Otawara (JP); Tomio Nabatame, Otawara (JP); Tomoko Suzuki, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 601 days.

(21) Appl. No.: 14/956,904

(22) Filed: Dec. 2, 2015

(65) Prior Publication Data
US 2016/0081653 A1 Mar. 24, 2016

Related U.S. Application Data

(63) Continuation of application No. PCT/JP2014/063662, filed on May 23, 2014.

(30) Foreign Application Priority Data

Jun. 11, 2013 (JP) .................................. 2013-122692
Apr. 2, 2014 (JP) .................................. 2014-076290

(51) Int. Cl.
*A61B 8/08* (2006.01)
*A61B 8/00* (2006.01)
(Continued)

(52) U.S. Cl.
CPC .......... *A61B 8/0841* (2013.01); *A61B 8/4254* (2013.01); *A61B 8/4263* (2013.01);
(Continued)

(58) Field of Classification Search
CPC ..... A61B 8/0841; A61B 8/4254; A61B 8/461; A61B 8/4263; A61B 8/5215;
(Continued)

(56) References Cited

U.S. PATENT DOCUMENTS

| 6,138,495 A | 10/2000 | Paltieli et al. |
| 6,311,540 B1 | 11/2001 | Paltieli et al. |
| 2002/0035864 A1 | 3/2002 | Paltieli et al. |
| 2005/0090742 A1 | 4/2005 | Mine et al. |

(Continued)

FOREIGN PATENT DOCUMENTS

| JP | 2001-526927 | 12/2001 |
| JP | 2005-58584 | 3/2005 |

(Continued)

OTHER PUBLICATIONS

English Translation of International Search Report dated Jun. 17, 2014 in PCT/JP2014/063662, filed on May 23, 2014.

*Primary Examiner* — Bo Joseph Peng
(74) *Attorney, Agent, or Firm* — Oblon, McClelland, Maier & Neustadt, L.L.P.

(57) ABSTRACT

According to one embodiment, an ultrasound diagnosis apparatus includes an ultrasound probe that transmits/receives ultrasound waves to/from a subject, a reference position member arranged on the ultrasound probe, and a sensor located in a position having a predetermined positional relationship relative to a puncture needle. The ultrasound diagnosis apparatus further includes a position information acquisition unit, a needle length information acquisition unit, and a display. The position information acquisition unit acquires position information of the reference position member and the sensor. The needle length information acquisition unit acquires needle length information indicating the length of the puncture needle based on the position information of the reference position member and the sensor when the tip of the puncture needle is in contact with the reference position member, and the relative posi- (Continued)

tion. The display displays information to guide a puncture by the puncture needle based on the needle length information.

12 Claims, 18 Drawing Sheets

(51) Int. Cl.
*A61B 17/34* (2006.01)
*A61B 90/00* (2016.01)
*A61B 34/20* (2016.01)

(52) U.S. Cl.
CPC ............ *A61B 8/461* (2013.01); *A61B 8/5215* (2013.01); *A61B 8/5223* (2013.01); *A61B 2017/3413* (2013.01); *A61B 2034/2051* (2016.02); *A61B 2034/2065* (2016.02); *A61B 2090/062* (2016.02); *A61B 2090/065* (2016.02)

(58) Field of Classification Search
CPC .......... A61B 8/5223; A61B 2034/2065; A61B 2034/2051; A61B 2017/3413; A61B 2090/062; A61B 2090/065
See application file for complete search history.

(56) References Cited

U.S. PATENT DOCUMENTS

| 2006/0063998 | A1* | 3/2006 | von Jako | A61B 5/06 600/407 |
| 2010/0298705 | A1* | 11/2010 | Pelissier | A61B 8/0833 600/443 |

FOREIGN PATENT DOCUMENTS

| JP | 2007-226 | 1/2007 |
| JP | 2007-215672 | 8/2007 |
| JP | 2008-149175 | 7/2008 |

* cited by examiner

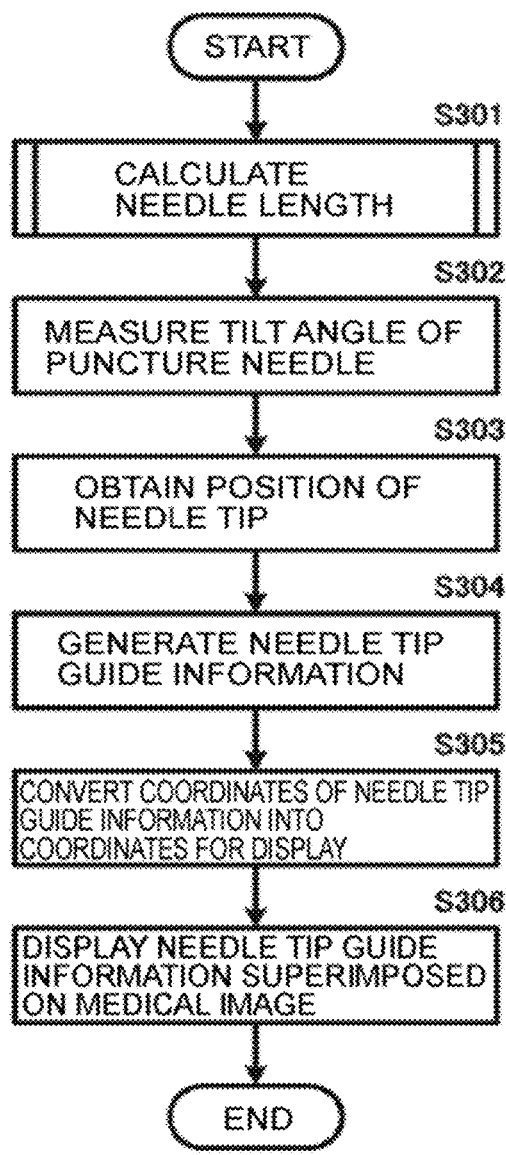

| THIRD POSITION | TILT ANGLE OF STRAIGHT LINE THAT CONNECTS SECOND POSITION AND THIRD POSITION, AND LENGTH OF STRAIGHT LINE |
|---|---|
| CENTER OF ACOUSTIC RADIATION SURFACE | $\alpha_1, \beta_1, \gamma_1, R_1$ |
| POSITION OF MARK | $\alpha_2, \beta_2, \gamma_2, R_2$ |

_US 10,363,013 B2_

ULTRASOUND DIAGNOSIS APPARATUS AND MEDICAL IMAGE DIAGNOSIS APPARATUS

CROSS-REFERENCE TO RELATED APPLICATION

This application is based upon and claims the benefit of priority from Japanese Patent Application No. 2013-122692, filed Jun. 11, 2013 and No. 2014-076290, filed Apr. 2, 2014; the entire contents of which are incorporated herein by reference.

FIELD

Embodiments described herein relate generally to an ultrasound diagnosis apparatus and a medical image diagnosis apparatus.

BACKGROUND

An ultrasound diagnosis apparatus, an X-ray computed tomography (CT) system, magnetic resonance imaging (MRI) equipment, and the like are used as a medical image diagnosis apparatus. Besides, there is a treatment called radio frequency ablation (RFA), in which a puncture needle is inserted into a subject to irradiate a tumor with radio waves or the like emitted from the tip of the puncture needle. It is not only in the RFA that the puncture needle is inserted into a subject. The puncture needle may be used to take samples of diseased tissue.

For example, when ablation therapy is performed with an ultrasound diagnosis apparatus, a position sensor is attached to each of an ultrasound probe and a puncture needle. The positions of the probe and the puncture needle are measured based on information from the position sensor. The position of the puncture needle is displayed on a two-dimensional image generated by the ultrasound diagnosis apparatus.

Thereby, the operator can navigate the puncture needle with reference to the two-dimensional image generated by the ultrasound diagnosis apparatus, and insert it into a puncture target site such as a tumor or the like. Besides, in the RFA, ablation of tumor tissue generates gas, which makes an ultrasound image less visible. Even in such a case, the operator can check the position of the puncture needle with reference to the navigation image.

In conventional puncture treatment, there is a case where a puncture needle is selected and a position sensor is attached thereto just before the puncture. In this case, the operator may arbitrarily determine a part of the puncture needle to attach the position sensor. The puncture needle to be used and the position to which the sensor is attached need to be changed according to the position (depth) of a diseased site. Accordingly, the attachment position of the sensor may not be determined until immediately before the puncture.

If the attachment position of the sensor is optional, the position of the puncture needle to which the sensor is attached cannot be determined only by information from the position sensor. Therefore, the operator is required to enter the attachment position of the sensor prior to the puncture operation. For this reason, if it is difficult to determine the attachment position of the position sensor in advance before the start of examination, the operator is required to manually enter information on the attachment position of the sensor during examination or surgery. This is very troublesome and imposes a heavy load on the operator.

BRIEF DESCRIPTION OF THE DRAWINGS

FIG. 14 is a flowchart illustrating a series of processes from the calculation of the needle length until the display of needle tip guide information;

FIG. 15 is a diagram illustrating a corresponding relationship between the tilt angle of a puncture needle and a third position;

DETAILED DESCRIPTION

Figure 1:
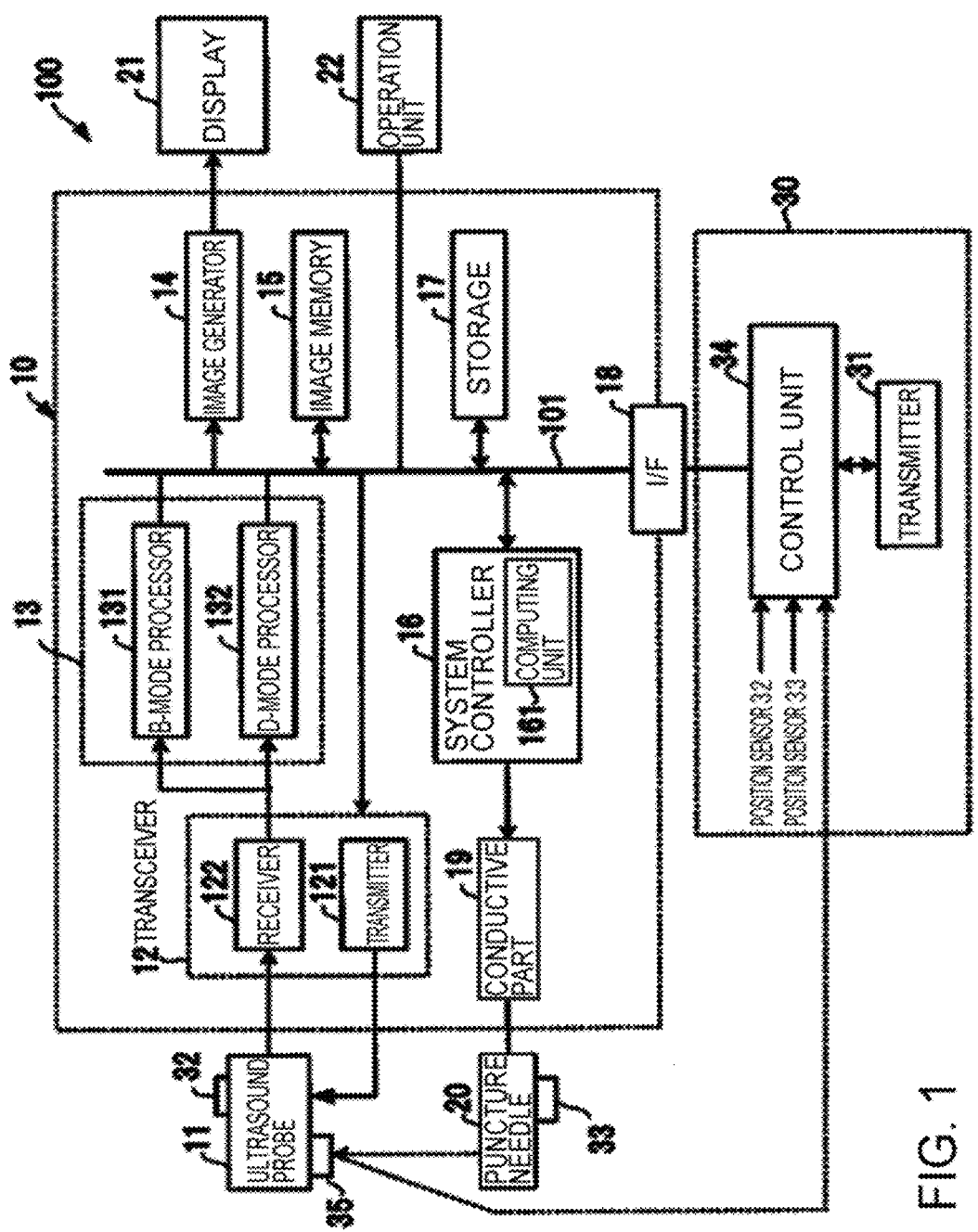
FIG. 1 is a block diagram of a medical image diagnosis apparatus according to a first embodiment.

In general, according to one embodiment, an ultrasound diagnosis apparatus includes an ultrasound probe that transmits/receives ultrasound waves to/from a subject, a reference position member arranged on the ultrasound probe, and a sensor located in a position having a predetermined positional relationship relative to a puncture needle. The ultrasound diagnosis apparatus further includes a position information acquisition unit, a needle length information acquisition unit, and a display. The position information acquisition unit acquires position information of the reference position member and the sensor. The needle length information acquisition unit acquires needle length information indicating the length of the puncture needle based on the position information of the reference position member and the sensor when the tip of the puncture needle is in contact with the reference position member, and the relative position. The display displays information to guide a puncture by the puncture needle based on the needle length information.

A description is given of an ultrasound diagnosis apparatus according to embodiments with reference to the drawings, in which like reference numerals designate like or corresponding parts throughout the various views.

First Embodiment

FIG. 1 is a block diagram illustrating the configuration of an ultrasound diagnosis apparatus 100 as a medical image diagnosis apparatus according to a first embodiment. As illustrated in FIG. 1, the ultrasound diagnosis apparatus 100 has a main body 10 that includes an ultrasound probe 11, a transceiver 12, and a data processor 13. The ultrasound probe 11 transmits and receives ultrasound waves to and from a subject (not illustrated). The transceiver 12 performs ultrasound scan of the subject by driving the ultrasound probe 11. The data processor 13 processes reception signals obtained by the transceiver 12 to generate image data such as B-mode image data, Doppler image data, and the like. The ultrasound probe 11, the transceiver 12, and the data processor 13 constitute an imaging unit for capturing a medical image by scanning a subject.

The main body 10 includes an image generator 14 configured to generate two-dimensional image data based on the image data output from the data processor 13, and an image memory 15 that stores the image data generated by the image generator 14. The main body 10 further includes a system controller 16 that controls the entire apparatus, a storage 17, an interface (I/F) 18, and a conductive part 19 configured to energize a puncture needle 20.

Besides, a display 21 and an operation unit 22 are connected to the main body 10. The display 21 is configured to display images and the like generated by the image generator 14. The operation unit 22 is used for entering various command signals and the like. Connected to the I/F 18 is a position information acquisition unit 30 (described in detail later). Incidentally, the system controller 16 is connected to each circuit via a bus line 101.

The ultrasound probe 11 is configured to transmit and receive ultrasound waves with its tip surface in contact with the body surface of the subject. The ultrasound probe 11 includes, for example, one-dimensional array of piezoelectric transducers. The piezoelectric transducers are electroacoustic transducers that convert an ultrasound drive signal to a transmission ultrasound wave at the time of transmitting and convert a received ultrasound wave from the subject to an ultrasound reception signal at the time of receiving. The ultrasound probe 11 is of, for example, sector type, linear type, or convex type. In the following, the ultrasound probe 11 is sometimes simply referred to as "probe".

The transceiver 12 includes a transmitter 121 configured to generate the ultrasound drive signal, and a receiver 122 configured to process the ultrasound reception signal obtained from the ultrasound probe 11. The transmitter 121 generates the ultrasound drive signal and outputs it to the ultrasound probe 11. The receiver 122 outputs the ultrasound reception signal (echo signal) from the piezoelectric transducers to the data processor 13.

The data processor 13 includes a B-mode processor 131 and a Doppler mode (D-mode) processor 132, which are configured to generate B-mode image data and Doppler image data, respectively, from the signal output from the transceiver 12. The B-mode processor 131 performs envelope detection on the signal from the transceiver 12, and then performs logarithmic transform thereon. The B-mode processor 131 converts the log-transformed signal into a digital signal to generate B-mode image data, and outputs the data to the image generator 14.

The D-mode processor 132 detects a Doppler shift frequency of the signal from the transceiver 12, and converts it to a digital signal. The D-mode processor 132 then extracts a blood flow, tissue, and contrast medium echo component due to Doppler effect to generate Doppler image data, and outputs the data to the image generator 14.

The image generator 14 generates an ultrasound image based on the B-mode image data, the Doppler image data, and the like output from the data processor 13. The image generator 14 includes a digital scan converter (DSC), and performs scan conversion of the generated image data to generate an ultrasound image (B-mode image, Doppler image, etc.) that can be displayed on the display 21.

The image memory 15 stores the image data generated by the image generator 14. The image data read out of the image memory 15 is output to the monitor 21. The image memory 15 also stores three-dimensional image data of other modalities (e.g., MPR image, etc.).

The system controller 16 controls the entire ultrasound diagnosis apparatus 100 to perform a variety of processes. For example, in response to various setting requests provided through the operation unit 22 or based on various control programs and various types of setting information read from the storage 17, the system controller 16 controls the operation of the transceiver 12, the data processor 13, and the image generator 14. The system controller 16 controls the display 21 to display an ultrasound image or the like stored in the image memory 15.

The storage 17 stores control programs for ultrasound transmission/reception, image processing and display processing, diagnostic information (e.g., subject ID, observations of doctors, etc.), and various data such as diagnostic protocols. In addition, the storage 17 is also used to store images stored in the image memory 15 as necessary. Further, the storage 17 stores various types of information used for processing by the system controller 16. The conductive part 19 is configured to cause a current to flow through the puncture needle 20, and supplies radio waves thereto.

The display 21 displays a graphical user interface (GUI) to allow the operator of the ultrasound diagnosis apparatus 100 to enter various setting requests by operating the operation unit 22. The display 21 also displays an ultrasound image generated in the main body 10 and a navigation image for puncture. The operation unit 22 includes an input device such as various switches, a keyboard, a track ball, a mouse, and a touch command screen. Various setting requests are received through the operation unit 22 from the operator, and sent to the main body 10.

The position information acquisition unit 30 is described below. The position information acquisition unit 30 acquires, for example, position information that indicates the position of the ultrasound probe 11 and the puncture needle 20. As the position information acquisition unit 30, for example, a magnetic sensor, an infrared sensor, an optical sensor, a camera, or the like can be used. In the following, the position information acquisition unit 30 is described as a magnetic sensor.

The position information acquisition unit 30 is a sensor using a magnetic field, and is a system including a transmitter 31, a plurality of position sensors 32 and 33, a control unit 34, and the system controller 16. The transmitter 31 is a source of the magnetic field. The position sensors 32 and 33 are configured to receive a reference signal from the transmitter 31. The control unit 34 controls the transmitter 31. The system controller 16 provides instructions to the control unit 34. Incidentally, the position sensors 32 and 33 may be hereinafter simply referred to as "sensor".

Using this system, the position sensors 32 and 33 are respectively attached to the ultrasound probe 11 and the puncture needle 20 to acquire the positional relationship between them and the distance information thereof from position information obtained by the two sensors 32 and 33. Although the position information acquisition unit 30 is not so limited, it is desirable to satisfy the following requirements.

That is, preferably, the position sensors 32 and 33 are six-axis sensors that acquire inclination information indicating how much each of the X, Y and Z axes is inclined from the reference axis of the magnetic field, and the offset distance from a reference point in the X, Y and Z directions using a magnetic field generating source as the reference point. From the distance and the inclination information, it is possible to know the position of the sensors in the space, and the direction in which the probe 11 and the puncture needle 20 are oriented.

The position sensor 32 is attached to the ultrasound probe 11 and fixed by using an adapter determined for each probe such that the orientation and the relative position from a reference position of the probe 11 are always constant. Similarly, the sensor 33 is attached to the puncture needle 20 by using an adapter. With the adapter, the orientation and the inclination of the sensor 33 relative to the puncture needle 20 are fixed. Thus, it is possible to know the direction in which the tip of the puncture needle 20 is located as viewed from the sensor 33. Preferably, the puncture needle 20 is linear and does not bend.

Figure 2:
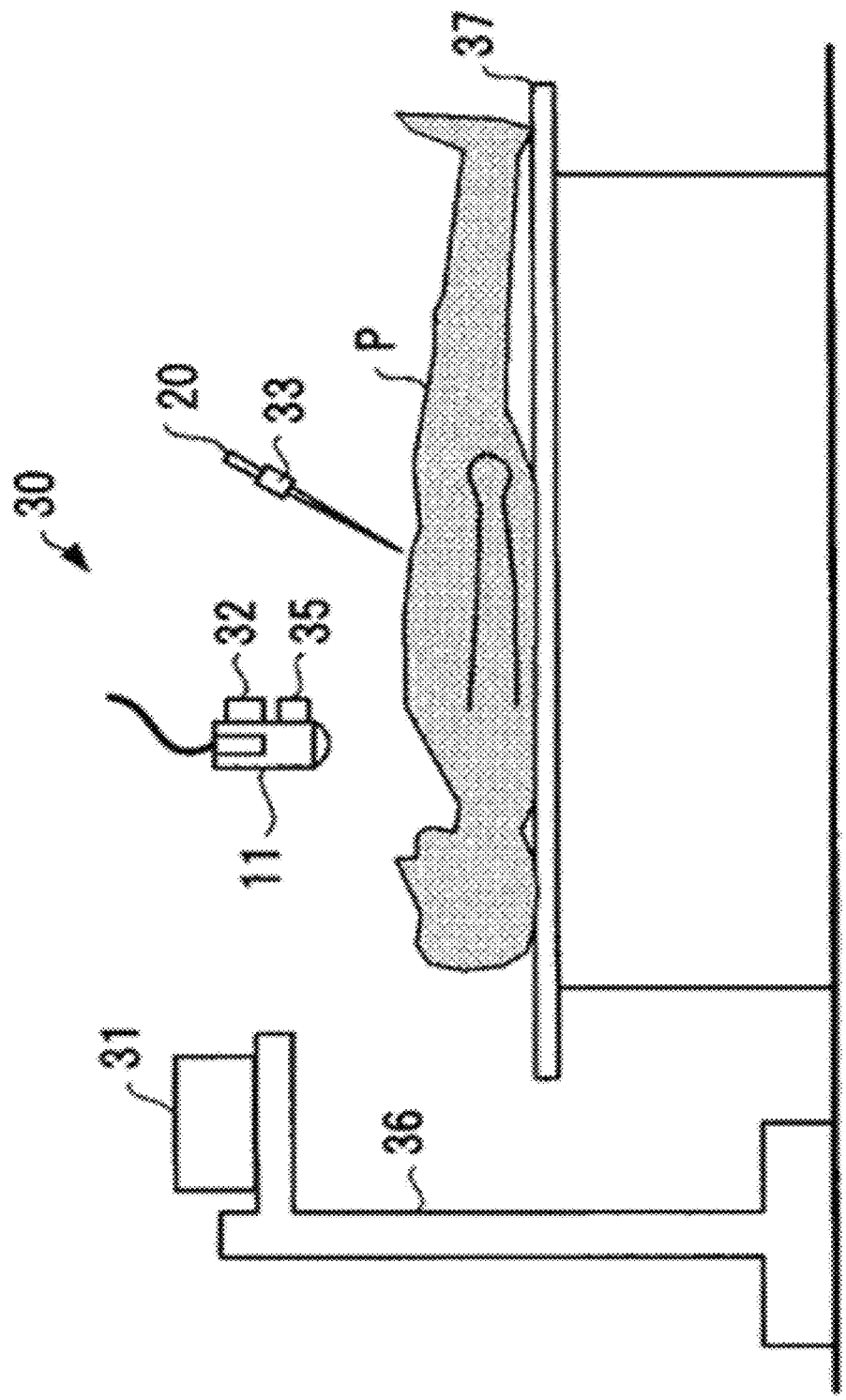
FIG. 2 is an explanatory view illustrating the arrangement of sensors of a position information acquisition unit of the first embodiment.

FIG. 2 is an explanatory view schematically illustrating the arrangement of the sensors in the position information acquisition unit 30. That is, the position information acquisition unit 30 includes the transmitter 31, the position sensors (receivers) 32 and 33, and the control unit 34. The transmitter 31 is attached to, for example, a pole 36 or the like in a fixed position near a bed 37 on which the subject P is placed.

The transmitter 31 transmits a reference signal to form a magnetic field around the apparatus toward the outside. In the three-dimensional field formed by the transmitter 31, the position sensors 32 and 33 each made of, for example, a magnetic sensor are arranged in an area in which magnetism transmitted from the transmitter 31 is receivable.

The position sensor 32 is attached to the ultrasound probe 11 as a support. The position sensor 32 receives the reference signal from the transmitter 31, and thereby acquires position information in the three-dimensional space, and detects the position and the orientation (inclination) of the probe 11. The position sensor 33 is attached to an arbitrary position of the puncture needle 20. By receiving the reference signal from the transmitter 31, the position sensor 33 acquires the position information in the three-dimensional space.

A conductor 35 is also attached to the ultrasound probe 11 (support). The conductor 35 is located in a position at a predetermined distance in a predetermined direction from the sensor 33. The control unit 34 controls the transmitter 31 to transmit magnetism. The control unit 34 obtains position information from the sensors 32 and 33 using the position of the transmitter 31 as a reference, and feeds it to the system controller 16.

For example, the tip of the puncture needle 20 can be brought in contact with the conductor 35. When the tip of the puncture needle 20 comes in contact with the conductor 35, the conductor 35 makes a weak current flow from the conductive part 19 through the puncture needle 20. Having detected that a current flows through the conductor 35, the control unit 34 automatically determines that the tip of the puncture needle 20 is located in the position of the conductor 35. That is, the conductor 35 is a sensitive element that reacts when the tip of the puncture needle 20 approaches within a distance set in advance.

The control unit 34 is connected to the system controller 16 through the I/F 18. The system controller 16 includes a computing unit 161. Based on information from the position sensors 32 and 33 and the conductor 35, the computing unit 161 calculates the distance between two points, i.e., the sensor 33 on the puncture needle 20 and the needle tip. In other words, the computing unit 161 calculates the needle length from the sensor 33 on the puncture needle 20 to the needle tip.

Figure 3:
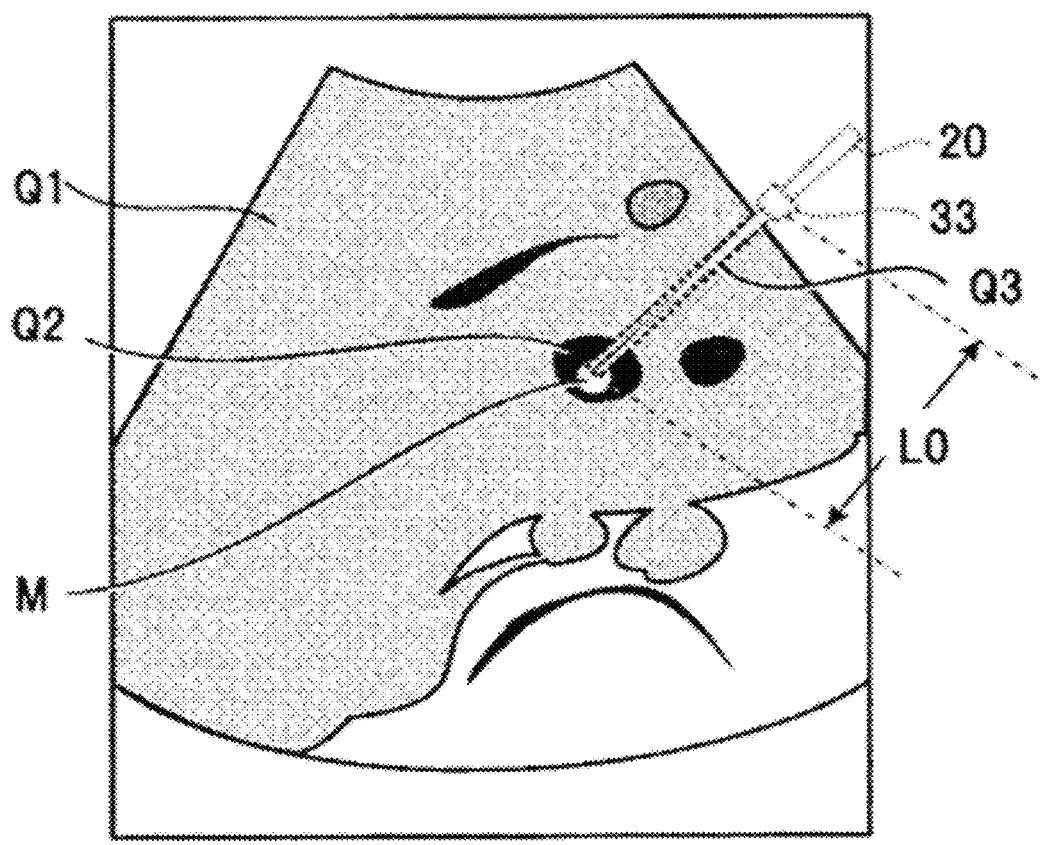
FIG. 3 is an explanatory view of an example of a medical image displayed on a display of the first embodiment.

FIG. 3 is an explanatory view of an example of a medical image displayed on the display 21 when ablation is performed by the puncture needle 20. Examples of the medical image include a navigation image for puncture and an ultrasound image. In the ablation therapy, first, the location of a tumor (puncture site) is checked by ultrasound diagnosis. More specifically, the target site of the subject P is scanned by the ultrasound probe 11 to sequentially acquire data of a two-dimensional tomographic image. The data is stored in the image memory 15. By sequentially storing data of two-dimensional tomographic images in the image memory 15, a three-dimensional image can be formed. The puncture site is specified based on the three-dimensional image.

FIG. 3 illustrates a two-dimensional tomographic image Q1 captured by the ultrasound probe 11, in which the location of a tumor (puncture site) is indicated by a black image Q2. The operator specifies the puncture site Q2 on the tomographic image Q1. The system controller 16 calculates a puncture direction and a puncture opening into which the puncture needle 20 is inserted, and the distance from the puncture opening to the puncture site.

Here, the operator selects the puncture needle 20, and attaches the sensor 33 to an arbitrary position (a position corresponding to needle length L0) of the puncture needle 20. Then, the operator brings the puncture needle 20 into contact with the conductor 35 to energize the conductor 35. With this energization, the computing unit 161 automatically calculates the two-point distance L0 between the sensor 33 on the puncture needle 20 and the needle tip, i.e., the needle length L0 from the sensor 33 on the puncture needle 20 to the needle tip. The system controller 16 displays a mark M that indicates the tip of the puncture needle at a position corresponding to the distance L0 as viewed from the puncture opening in the puncture direction.

The position sensor 33 can provide information that indicates the direction in which the tip of the puncture needle 20 is directed. Therefore, when the puncture opening for the puncture needle 20 is determined, the system controller 16 displays a guide image Q3 extending from the sensor 33 to the needle tip as a navigation image for puncture, and also displays the mark M at the position of the needle tip.

While viewing the guide image Q3 of FIG. 3, the operator inserts the puncture needle 20 towards the puncture site Q2. As the puncture needle 20 is inserted, an image of the puncture needle 20 is displayed on the tomographic image Q1. Having checked that the tip of the puncture needle 20 reaches the mark M (puncture site Q2), the operator gives an instruction, for example, to irradiate tumor tissue with radio waves emitted from the tip of the puncture needle 20 to ablate it. The radio waves are supplied from the conductive part 19 to the puncture needle 20.

Figure 4:
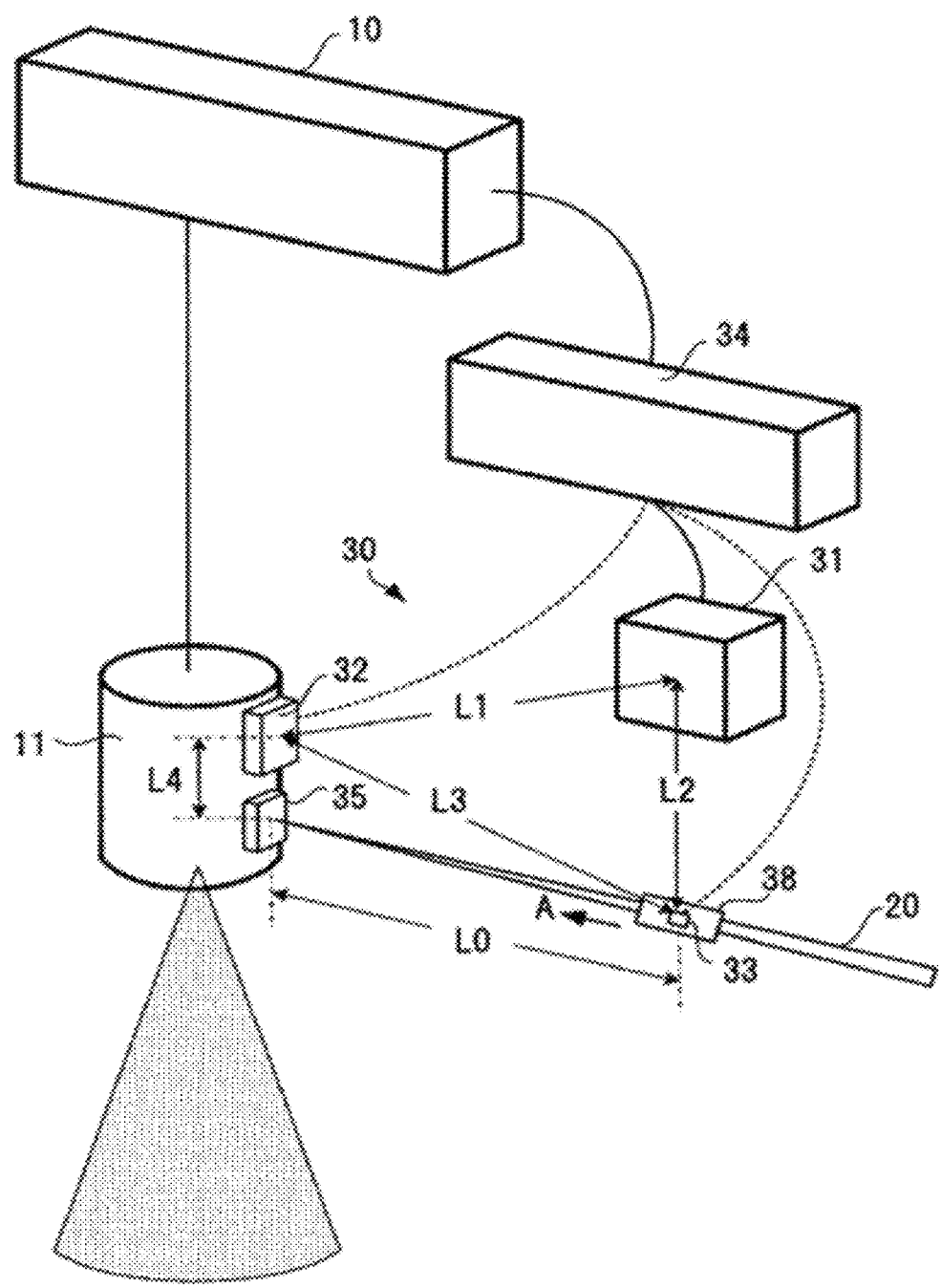
FIG. 4 is a diagram illustrating the schematic configuration of the position information acquisition unit of the first embodiment.

FIG. 4 is a diagram illustrating the schematic configuration of the position information acquisition unit 30. FIG. 4 also serves as an explanatory diagram for the operation of calculating the needle length L0 from the sensor 33 on the puncture needle 20 to the needle tip. FIG. 4 illustrates the enlarged view of the main body 10 of the ultrasound diagnosis apparatus, the position information acquisition unit 30, the ultrasound probe 11, and the puncture needle 20. The position information acquisition unit 30 includes, in addition to the control unit 34 and the transmitter 31, the position sensor 32 attached to the ultrasound probe 11, the conductor 35, and the position sensor 33 attached to the puncture needle 20.

An adapter 38 is attached to the puncture needle 20, and the sensor 33 is fixed to the adapter 38. The adapter 38 is attached to the puncture needle 20 such that it can be seen which direction the needle tip is located as viewed from the sensor 33. In the example of FIG. 4, arrow A indicates the direction of the needle tip.

In FIG. 4, when performing a puncture, the operator (doctor, etc.) determines the puncture needle 20 and the type of the ultrasound probe 11 according to the target site to be examined or treated. The operator then attaches the adapter 38 to an arbitrary position of the puncture needle 20, and determines the attachment position of the sensor 33. After that, the operator turns on a navigation switch on the operation unit 22 to operate in the navigation mode for guiding the insertion of the puncture needle.

After the navigation switch is turned on, a weak current flows from the conductive part 19 through the puncture needle 20 for a certain period of time. When the operator brings the tip of the puncture needle 20 into contact with the conductor 35 arranged on the probe 11, an electrical circuit is formed, and a current flows through the conductor 35 via the puncture needle 20. When a current flows through the conductor 35, the system controller 16 recognizes that the tip of the puncture needle 20 is located in the position of the conductor 35, and automatically calculates the needle length L0 as described above.

As illustrated in FIG. 4, the control unit 34 obtains the position information of the sensors 32 and 33 (information indicating the distance and direction from the transmitter 31), and sends it to the system controller 16. Thereby, the computing unit 161 of the system controller 16 calculates the distance L1 between the transmitter 31 and the sensor 32, the distance L2 between the transmitter 31 and the sensor 33, and the distance L3 between the sensors 32 and 33. Since the distance L4 between the position sensor 32 and the conductor 35 has been found in advance, the distance L0 between the position sensor 33 and the conductor 35 (the needle length L0 from the position sensor 33 on the puncture needle 20 to the needle tip) can be calculated.

Thus, by only bringing the tip of the puncture needle 20 into contact with the conductor 35, the operator can make the computing unit 161 automatically measure the needle length L0 of the puncture needle 20. The system controller 16 controls the display of the mark M such that it is displayed at the position of the tip of the puncture needle in FIG. 3 based on the information of the needle length L0. With this, the display position of the mark M can be made accurate.

Further, the operator can dispense with manually entering information on the needle length L0, which simplifies the operation during the examination, resulting in less load on the operator. Since the needle length L0 is changed according to the depth of a diseased site, the operability can be improved by automatically measuring the information of the needle length L0.

Figure 5:
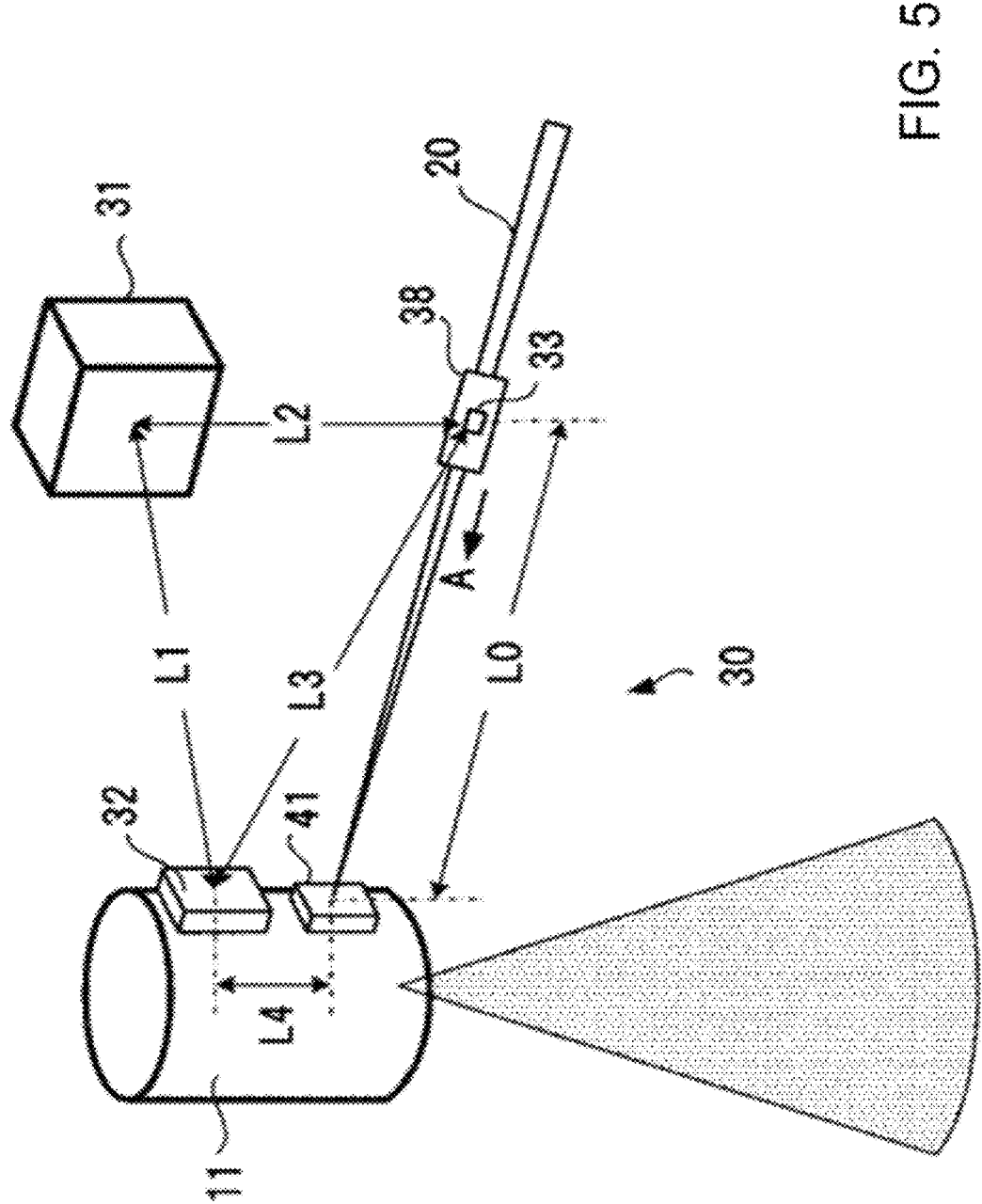
FIG. 5 is a diagram illustrating the schematic configuration of a position information acquisition unit according to a first modification of the first embodiment.

Next, a description is given of a medical image diagnosis apparatus according to modifications of the first embodiment. FIG. 5 is a diagram illustrating the schematic configuration of the position information acquisition unit 30 according to a first modification. FIG. 5 illustrates an example in which a pressure-sensitive sensor 41 is attached to the ultrasound probe 11 in place of the conductor 35. The position sensor 32 and the pressure-sensitive sensor 41 are attached to the probe 11. The distance L4 between the position sensor 32 and the pressure-sensitive sensor 41 is designated in advance. The pressure-sensitive sensor 41 constitutes a sensitive element that reacts when the tip of the puncture needle 20 approaches within a distance set in advance (comes in contact therewith).

As illustrated in FIG. 5, the control unit 34 obtains the position information of the sensors 32 and 33 (information indicating the distance and direction from the transmitter 31), and sends it to the system controller 16. Thereby, the computing unit 161 of the system controller 16 calculates the distance L1 between the transmitter 31 and the sensor 32, the distance L2 between the transmitter 31 and the sensor 33, and the distance L3 between the sensors 32 and 33.

When the operator brings the tip of the puncture needle 20 into contact with the pressure-sensitive sensor 41 and presses it lightly, the pressure sensitive sensor 41 exhibits a reaction. In response to the reaction of the pressure sensitive sensor 41, the control unit 34 recognizes that the tip of the puncture needle 20 is in the position of the pressure-sensitive sensor 41. Since the distance L4 between the position sensor 32 and the pressure-sensitive sensor 41 is set in advance, in response to that the pressure-sensitive sensor 41 has sensed the needle tip, the computing unit 161 automatically calculates the distance L0 between the sensor 33 and the pressure-sensitive sensor 41 (the needle length L0 from the position sensor 33 on the puncture needle 20 to the needle tip).

Figure 6:
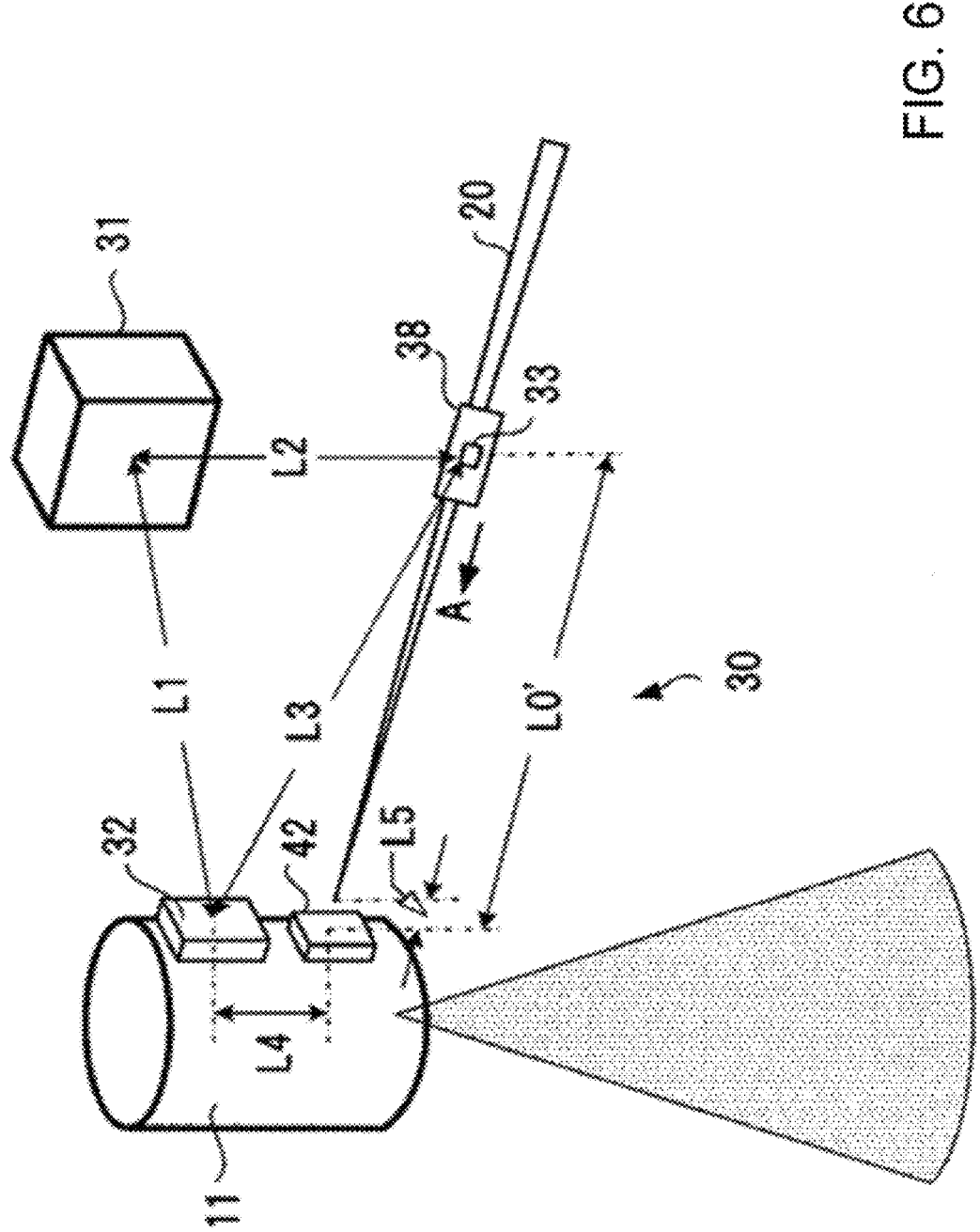
FIG. 6 is a diagram illustrating the schematic configuration of a position information acquisition unit according to a second modification of the first embodiment.

FIG. 6 is a diagram illustrating the schematic configuration of the position information acquisition unit 30 according to a second modification. FIG. 6 illustrates an example in which a proximity sensor 42 is attached to the ultrasound probe 11 in place of the conductor 35. The position sensor 32 and the proximity sensor 42 are attached to the probe 11. The distance L4 between the position sensor 32 and the proximity sensor 42 is designated in advance. The proximity sensor 42 constitutes a sensitive element that reacts when the tip of the puncture needle 20 approaches within a distance set in advance.

As illustrated in FIG. 6, the control unit 34 obtains the position information of the sensors 32 and 33 (information indicating the distance and direction from the transmitter 31), and sends it to the system controller 16. Thereby, the computing unit 161 calculates the distance L1 between the transmitter 31 and the sensor 32, the distance L2 between the transmitter 31 and the sensor 33, and the distance L3 between the sensors 32 and 33.

When the operator brings the tip of the puncture needle 20 close to the proximity sensor 42, and the needle tip approaches within a proximity distance L5 set in advance, the proximity sensor 42 exhibits a reaction. In response to the reaction of the proximity sensor 42, the control unit 34 recognizes that the needle tip approaches the proximity sensor 42. Since the distance L4 between the sensor 32 and the proximity sensor 42 is set in advance, in response to that the proximity sensor 42 has sensed the needle tip, the computing unit 161 automatically calculates the two-point distance L0' between the sensor 33 and the proximity sensor 42. Because the tip of the puncture needle is not actually in contact with the proximity sensor 42, the proximity distance L5 is subtracted from the distance L0' calculated. Thus, the needle length L0 from the sensor 33 on the puncture needle 20 to the needle tip can be obtained.

As another modification, a three-dimensional camera may be attached in place of the proximity sensor 42. The position sensor 32 and the three-dimensional camera are attached to the probe 11. The distance between the position sensor 32 and the three-dimensional camera is designated in advance.

When the operator brings the tip of the puncture needle 20 close to the front of the three-dimensional camera, the three-dimensional camera recognizes the image of the tip of the puncture needle 20. The control unit 34 informs the system controller 16 of the result of the image recognition by the three-dimensional camera. The computing unit 161 of the system controller 16 recognizes that the needle tip approaches within a close distance to the three-dimensional camera. Thus, the computing unit 161 automatically calculates the needle length from the sensor 33 on the puncture needle 20 to the needle tip similarly to the case of FIG. 6.

As described above, in the first embodiment, puncture, RFA treatment, and the like can be performed under the guide of the navigation image. Further, the operator is not required to manually enter information on the needle length. Thus, the settings can be made easily and quickly.

Second Embodiment

Next, a description is given of a medical image diagnosis apparatus according to a second embodiment. The medical image diagnosis apparatus of the second embodiment relates to an X-ray CT apparatus.

Figure 7:
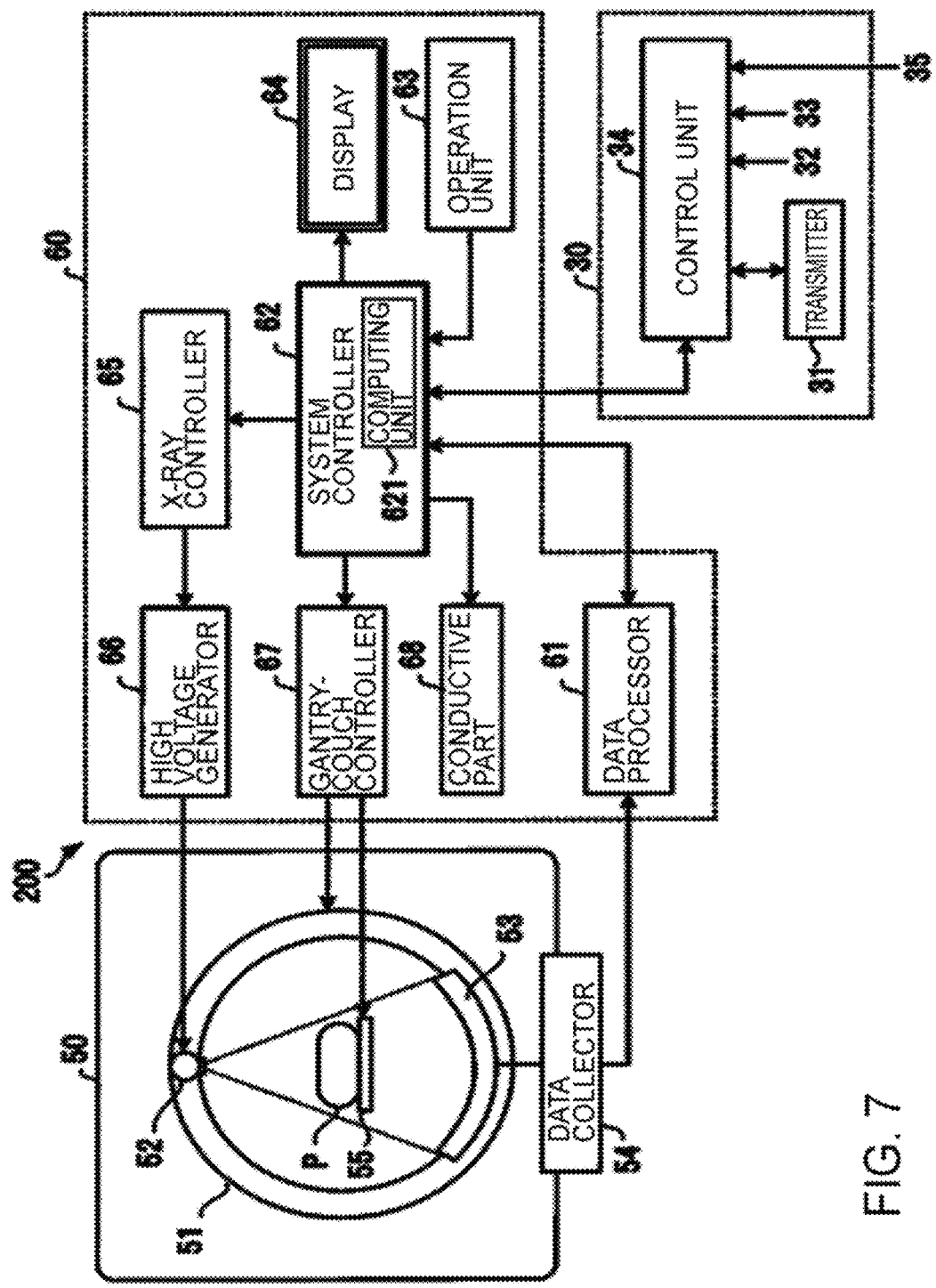
FIG. 7 is a block diagram of a medical image diagnosis apparatus according to a second embodiment.

FIG. 7 is a block diagram of an X-ray CT apparatus 200 according to the second embodiment. The X-ray CT apparatus 200 includes a frame 50 and a computer system 60. The frame 50 is intended to collect projection data relating to the subject P, and includes a rotatable frame 51, an X-ray tube 52, an X-ray detector 53, and a data collector corrector.

The rotatable frame 51 is a ring which is rotationally driven. The rotatable frame 51 has the X-ray tube 52 and the X-ray detector 53 mounted thereon. The center part of the rotatable frame 51 is opened such that the subject P placed on a top plate 55 of a bed 56 (FIG. 8) is inserted into the opening.

The X-ray tube 52 is supplied with power (tube current, tube voltage) required for X-ray irradiation from a high voltage generator 66 through a slip ring (described later), and irradiates X-rays to the subject P placed within an effective visual field. The X-ray detector 53 detects X-rays transmitted through the subject P. The X-ray detector 53 is attached to the rotatable frame 51 to face the X-ray tube 52. The X-ray detector 53 is, for example, a multi-slice type detector, in which a plurality of X-ray detection elements are two-dimensionally arranged in multiple rows in the channel direction and the slice direction.

The frame 50 including the X-ray tube 52 and the X-ray detector 53, the top plate 55, and the bed 56 constitute an imaging unit for capturing a medical image by scanning a subject. With the rotation of the rotatable frame 51, the X-ray tube 52 and the X-ray detector 53 rotate substantially about the body axis of the subject P while facing each other. In addition, if the top plate 55 is controlled to move along the body axis direction of the subject P simultaneously with the rotation of the rotatable frame 51, so-called helical scan to scan the subject in a spiral pattern can be performed.

A data collector 54 is called data acquisition system (DAS). The data collector 54 converts a signal output from the X-ray detector 53 for each channel into a voltage signal, and amplifies it into a digital signal. The digital data is sent to the computer system 60.

The computer system 60 includes a data processor 61, a system controller 62, an operation unit 63, a display 64, an X-ray controller 65, the high voltage generator 66, a gantry-couch controller 67, and a conductive part 68. The data processor 61 includes a pre-processor, a reconstruction unit, and a storage or the like. Having received raw data (projection data) from the data collector 54, the data processor 61 performs reconstruction processing or the like after preprocessing.

The data processor 61 is equipped with, for example, a plurality of kinds of reconstruction methods, and reconstructs image data according to a reconstruction method selected by the operator. The image data reconstructed is then subjected to window transformation and image processing for display such as RGB processing. According to an instruction from the operator, the data processor 61 generates a tomographic image of an arbitrary cross section, a projection image from an arbitrary direction, a three-dimensional image, or the like. The image data such as tomographic image thus reconstructed is stored in a storage in the data processor 61.

The system controller 62 performs the overall control of the X-ray CT apparatus 200 to perform scan processing, signal processing, image display processing, and the like. Besides, the system controller 62 generates a navigation image for puncture. The system controller 62 includes a computing unit 621. The operation unit 63 includes a keyboard, various switches, a mouse, and the like to allow the operator to select a slice to be observed or to enter various scan conditions such as a slice thickness and the number of slices. The display 64 displays medical images obtained by the data processor 61, a navigation image for puncture, and the like under the control of the system controller 62.

The X-ray controller 65 controls the high voltage generator 66 to supply the X-ray tube 52 with power required for X-ray irradiation through the slip ring. The gantry-couch controller 67 rotates the rotatable frame 51 as well as controlling the movement of the bed 56 (FIG. 8) and the top plate 55. The conductive part 68 is configured to cause a current to flow through the puncture needle 20, and supplies radio waves thereto.

The position information acquisition unit 30 is connected to the system controller 62. The position information acquisition unit 30 includes, as illustrated in FIG. 1, the transmitter 31, the position sensors (receivers) 32 and 33, and the control unit 34. Having detected that a current flows through the conductor 35, the control unit 34 automatically determines that the tip of the puncture needle 20 is located in the position of the conductor 35.

Figure 8:
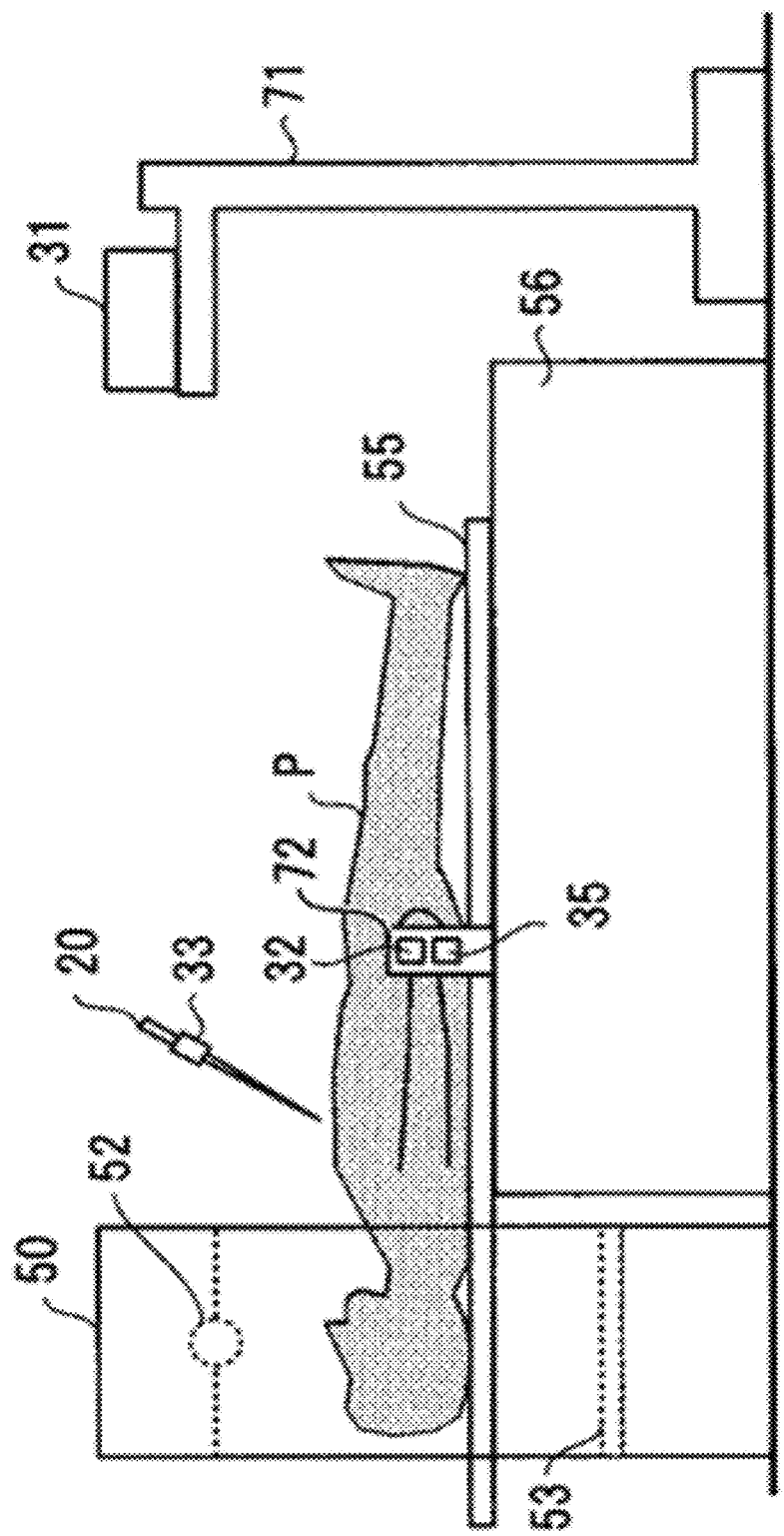
FIG. 8 is an explanatory view illustrating the arrangement of a sensor of a position information acquisition unit of the second embodiment.

FIG. 8 is an explanatory view schematically illustrating the arrangement of the position information acquisition unit 30 in the second embodiment. FIG. 8 illustrates the arrangement of the transmitter 31, the position sensors 32 and 33, and the conductor 35. As illustrated in FIG. 8, the transmitter 31 is attached to, for example, a pole 71 or the like in a fixed position near the bed 56 on which the subject P is placed. In the three-dimensional field formed by the transmitter 31, the position sensors 32 and 33 each made of, for example, a magnetic sensor are arranged in an area in which magnetism transmitted from the transmitter 31 is receivable. Incidentally, the position sensors 32 and 33 may be hereinafter simply referred to as "sensor".

The sensor 32 is attached to, for example, a support 72 which is fixed to the bed 56. The sensor 33 is attached to an arbitrary position of the puncture needle 20. The conductor 35 is also attached to the support 72. The conductor 35 is located in a position at a predetermined distance from the sensor 32.

The control unit 34 controls the transmitter 31 to transmit magnetism. The control unit 34 obtains position information from the sensors 32 and 33 using the position of the transmitter 31 as a reference, and feeds it to the system controller 16.

The tip of the puncture needle 20 can be brought in contact with the conductor 35. When the tip of the puncture needle 20 comes in contact with the conductor 35, the conductor 35 makes a weak current flow from the conductive part 68 through the puncture needle 20. Having detected that a current flows through the conductor 35, the control unit 34 automatically determines that the tip of the puncture needle 20 is located in the position of the conductor 35. Besides, the computing unit 621 of the system controller 62 calculates the needle length from the sensor 33 on the puncture needle 20 to the needle tip based on information from the sensors 32 and 33, and the conductor 35.

Figure 9:
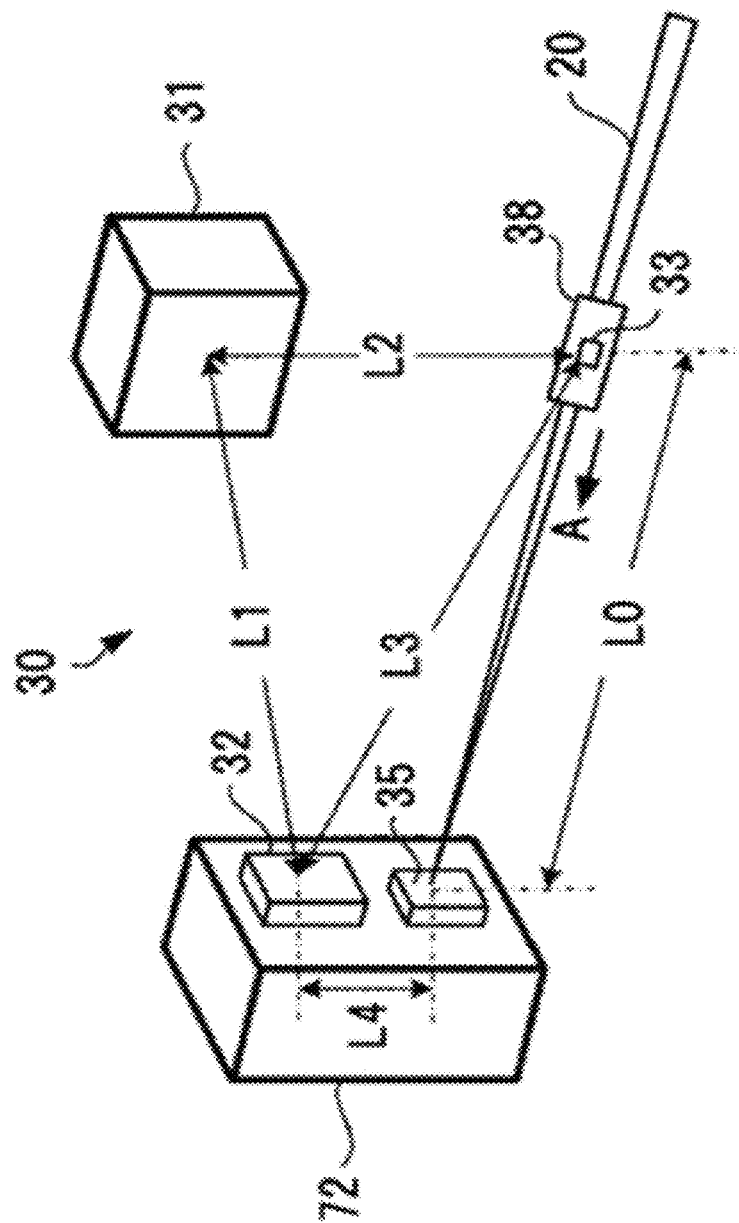
FIG. 9 is a diagram illustrating the schematic configuration of the position information acquisition unit of the second embodiment.

FIG. 9 is a diagram illustrating the schematic configuration of the position information acquisition unit 30. FIG. 9 also serves as an explanatory diagram for the operation of calculating the needle length L0. The adapter 38 is attached to the puncture needle 20, and the sensor 33 is fixed to the adapter 38. The adapter 38 is attached to the puncture needle 20 such that it can be seen which direction the needle tip is located as viewed from the sensor 33. In the example of FIG. 9, arrow A indicates the direction of the needle tip.

In FIG. 9, when the operator brings the tip of the puncture needle 20 into contact with the conductor 35 arranged on the support 72, an electrical circuit is formed, and a current flows through the conductor 35 via the puncture needle 20. With this, the computing unit 621 recognizes that the tip of the puncture needle 20 is located in the position of the conductor 35, and automatically calculates the two-point distance L0 between the sensor 33 and the needle tip.

That is, the computing unit 621 calculates the distance L1 between the transmitter 31 and the sensor 32, the distance L2 between the transmitter 31 and the sensor 33, and the distance L3 between the sensors 32 and 33. Since the distance L4 between the position sensor 32 and the conductor 35 has been set in advance, the distance L0 between the position sensor 33 and the conductor 35 (the needle length L0 from the position sensor 33 on the puncture needle 20 to the needle tip) can be calculated.

Thus, by only bringing the tip of the puncture needle 20 into contact with the conductor 35, the operator can make the computing unit 621 automatically measure the needle length L0 from the position sensor 33 on the puncture needle 20 to the needle tip.

The navigation for the puncture needle 20 by the X-ray CT apparatus 200 is performed, for example, as follows: Using the operation unit 63, the operator determines a target site to be treated while observing a fluoroscopic image of the subject P. Next, the operator captures an image of the target site to be treated, and acquires volume data. Then, the operator reconstructs a volumetric image of the subject and displays it on the display 64. While viewing the display image, the operator specifies a target (the target site to be treated) in the volume image, and specifies an insertion position of the puncture needle 20.

The system controller 62 calculates a puncture direction and a puncture opening into which the puncture needle 20 is inserted, and the distance from the puncture opening to the puncture site. Here, the operator selects the puncture needle 20, and attaches the sensor 33 to an arbitrary position (a position corresponding to needle length L0) of the puncture needle 20. Then, the operator brings the puncture needle 20 into contact with the conductor 35 to energize the conductor 35. With this energization, the computing unit 621 automatically calculates the needle length L0 from the sensor 33 on the puncture needle 20 to the needle tip. The system controller 62 displays the mark M that indicates the tip of the puncture needle at a position corresponding to the distance L0 as viewed from the puncture opening in the puncture direction.

The position sensor 33 can provide information that indicates the direction in which the tip of the puncture needle 20 is directed. Therefore, when the puncture opening for the puncture needle 20 is determined, the system controller 62 displays a guide image extending from the sensor 33 to the needle tip as a navigation image for puncture, and also displays the mark M at the position of the needle tip.

While viewing the guide image, the operator inserts the puncture needle 20 towards the puncture site (mark). The operator gives an instruction, for example, to irradiate tumor tissue with radio waves emitted from the tip of the puncture needle 20 to ablate it. The radio waves are supplied from the conductive part 68 to the puncture needle 20.

According to the second embodiment, the system controller 62 controls the display of the mark indicating the tip of the puncture needle such that it is displayed based on the information of the needle length L0. With this, the display position of the mark M can be made accurate. Further, the operator can dispense with manually entering information on the needle length L0, which simplifies the operation during the examination, resulting in less load on the operator.

Note that, in the second embodiment, the pressure-sensitive sensor 41, the proximity sensor 42, or the camera as described in the modifications of the first embodiment may be used in place of the conductor 35, In addition, although the second embodiment is described by taking the X-ray CT apparatus as an example, the navigation by measuring the needle length between the position sensor 33 and the needle tip of the puncture needle 20 can be applicable to X-ray imaging apparatuses such as MRI apparatuses and angiography apparatuses, and other medical image diagnosis apparatuses. Further, while an example is described in which the puncture needle 20 is inserted into the subject to cauterize a diseased site, the embodiment can also be applicable to the case where the puncture needle for tissue collection is inserted into the subject to obtain the tissue of the diseased site.

(Another Example of the Attachment Position of the Sensor 33)

While, in the above embodiment, the sensor 33 is attached to the puncture needle 20, the attachment position of the sensor 33 is not limited to the puncture needle 20. The sensor 33 may be located in any position as long as it has a predetermined positional relationship relative to the puncture needle 20. For example, the sensor 33 may be located in a holder (not illustrated) or the main body 10 of the ultrasound diagnosis apparatus 100. In this case, for example, a needle length information acquisition unit acquires the position information of the puncture needle 20 based on the position information of the sensor 33 when the tip of the puncture needle is in contact with a reference position member with reference to the relative position. With further reference to the position information of the reference position member, the needle length information acquisition unit acquires information on the length of the puncture needle.

Third Embodiment

In the above embodiments, to obtain the needle length of the puncture needle 20, it is detected that the tip of the puncture needle 20 is located in a predetermined position by using the conductor 35, the pressure-sensitive sensor 41, the proximity sensor 42, and the camera. However, it is not limited thereto. Described below is a method of obtaining the needle length without using the conductor 35 and the like, in which, when the tip of the puncture needle is aligned in a predetermined position, the operator instructs the measurement through the input unit (not illustrated).

In paracentesis (puncture treatment), to enter the needle length easily and precisely, the structure of the medical image diagnosis apparatus of the embodiment is as follows: (1) For example, a magnetic sensor is arranged in a first position of the puncture needle. (2) A predetermined position is provided in the imaging unit (a unit other than the puncture needle in the medical image diagnosis apparatus). (3) The tip of the puncture needle (needle tip) is aligned in the predetermined position. (4) At this time, a position measurement system measures the first position and the predetermined position. (5) The distance between the first position and the predetermined position is obtained as the needle length based on the first position and the predetermined position measured.

Here, a description that "a position measurement system measures the first position and the predetermined position" indicates to directly measure the predetermined position by a position measurement system (hereinafter referred to as "direct measurement"), including to measure a position other than the predetermined position, thereby obtaining the predetermined position from the measured value (hereinafter referred to as "indirect measurement").

The predetermined position can be directly measured by, for example, arranging a magnetic sensor in the predetermined position, and measuring the predetermined position by the position measurement system. In this case, however, it is not clear where of the magnetic sensor arranged in the predetermined position the needle tip is to be aligned in. Accordingly, if the needle tip aligned in the predetermined position deviates therefrom, the needle length may not be measured accurately. For this reason, a position ("third position" described later) having a predetermined positional relationship with the position where the magnetic sensor is arranged is provided to measure the needle length accurately by aligning the needle tip in the position.

In a third embodiment, the indirect measurement is described. Note that the position of the puncture needle where a magnetic sensor is arranged is referred to as "first position". The position in an imaging unit where a magnetic sensor is arranged is referred to as "second position". A position having a predetermined positional relationship with the second position is referred to as "third position". Here, the first position is a position where a first measurement object (magnetic sensor 310 described later) is arranged. The second position is a position where a second measurement object (magnetic sensor 320 described later) is arranged.

Further, in the third embodiment, an example is described in which guide information is created based on the needle length obtained, and is displayed as being superimposed on an echo image.

Figure 10:
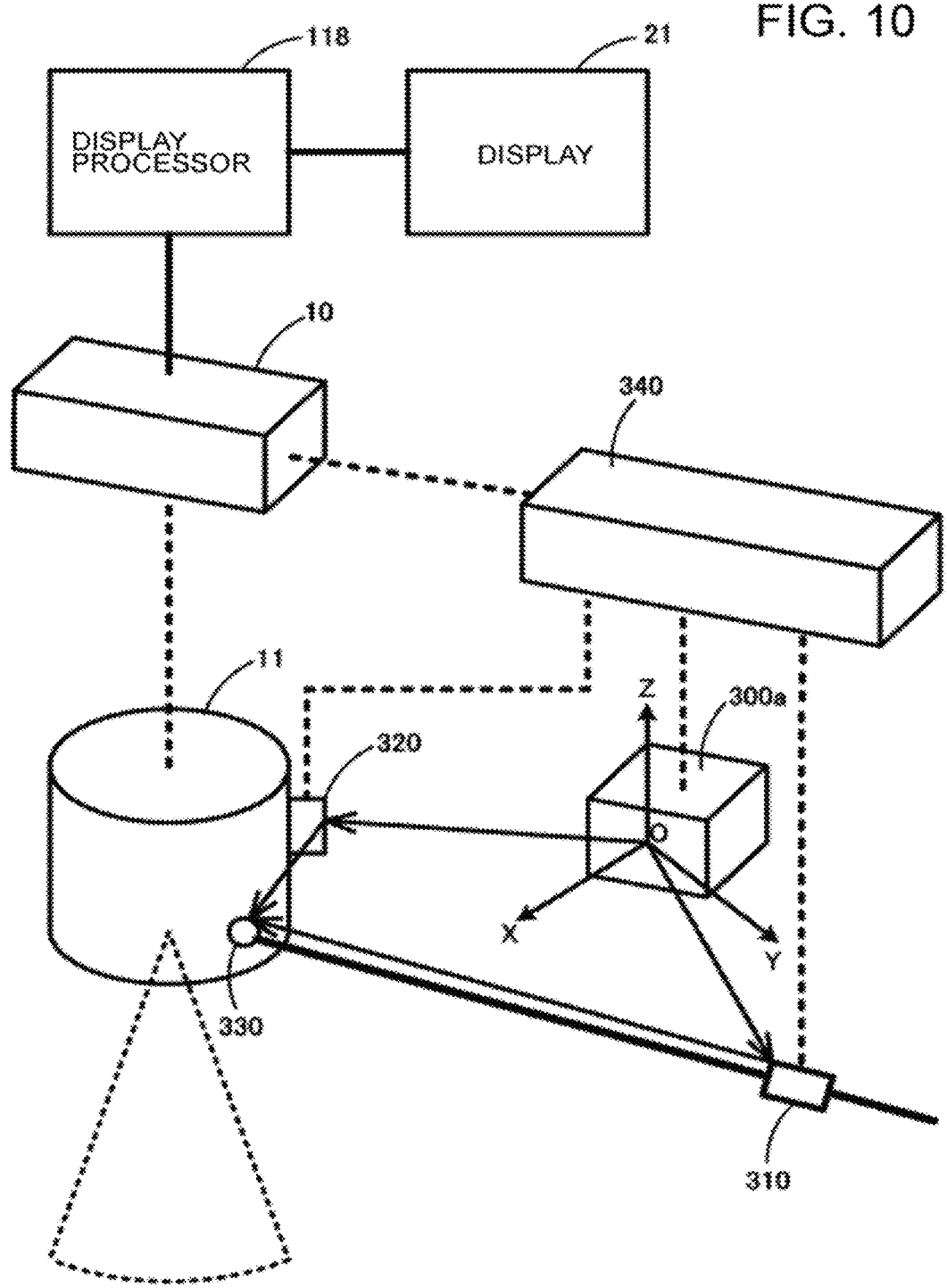
FIG. 10 is a diagram of an ultrasound diagnosis apparatus according to a third embodiment.

A description is given of a medical image diagnosis apparatus according to the third embodiment with reference to the drawings. FIG. 10 is a diagram illustrating the schematic configuration of a medical image diagnosis apparatus according to the third embodiment. In this embodiment, an ultrasound diagnosis apparatus is described as the medical image diagnosis apparatus.

As illustrated in FIG. 10, the ultrasound diagnosis apparatus includes the ultrasound probe 11, a position measurement system 300 (see FIG. 11), a needle length information acquisition unit 100A, a display processor 118, and the display 21. The ultrasound probe 11 is an example of "imaging unit". The position measurement system 300 is an example of "position information acquisition unit".

(Position Measurement System 300)

The position measurement system 300 includes a magnetic field generating source (transmitter) 300a, magnetic sensors 310 and 320 that sense a change in the magnetic field, and a control unit 340 that control them. The position measurement system 300 performs measurement in response to an instruction from the user. The user provides the instruction using the input device (not illustrated) by manually bringing the needle tip (front end of the puncture needle) into contact with the third position 330. The needle length is determined based on the measured result.

The magnetic field generating source 300a is arranged in the periphery of the ultrasound diagnosis apparatus. The position where the magnetic field generating source 300a is located servers as the origin of the XYZ coordinates. The magnetic field generating source 300a includes orthogonal coils in three directions. The magnetic sensors 310 and 320 also include orthogonal coils in three directions. When the three coils of the magnetic field generating source 300a are excited in order, electromotive force is sequentially generated in the three coils of the magnetic sensors 310 and 320.

The magnetic sensor 310 is arranged in the first position of the puncture needle through an adapter (not illustrated). Based on a signal (the electromotive force) from the magnetic sensor 310 that has received a change in the magnetic field caused by the magnetic field generating source 300a, the XYZ coordinates of the first position $(x_1, y_1, z_1)$ and the tilt angles $(\lambda, \mu, \omega)$ of the puncture needle are measured. Here, $\lambda$, $\mu$ and $\omega$ are the tilt angles of the puncture needle with respect to the X-axis, the Y-axis, and the Z-axis.

The magnetic sensor 320 is arranged in the second position of the ultrasound probe 11. Based on a signal (the electromotive force) from the magnetic sensor 320 that has received a change in the magnetic field caused by the magnetic field generating source 300a, the XYZ coordinates $(x_2, y_2, z_2)$ of the second position and the tilt angles $(\theta, \delta, \varphi)$ of the ultrasound probe 11 are measured. The coordinates using the second position of the ultrasound probe 11 as its origin are referred to as UVW coordinates. Here, the tilt angles of the ultrasound probe 11 indicate the inclination of the UVW coordinates with respect to the XYZ coordinates. To match the UVW coordinates with the XYZ coordinates, the UVW coordinates are rotated about the U-axis, the V-axis and the W-axis, respectively, by θ, δ and φ degrees. The tilt angle of the ultrasound probe 11 is an example of "tilt angle of the imaging unit".

As described above, the position measurement system 300 measures the first position of the puncture needle, the tilt angles, the second position of the ultrasound probe 11, and the tilt angles. The ultrasound probe 11 is provided with a third position having a predetermined positional relationship with the second position. The positional relationship is stored in a storage 116 (described later).

[Needle Length Information Acquisition Unit 100A]

Figure 11:
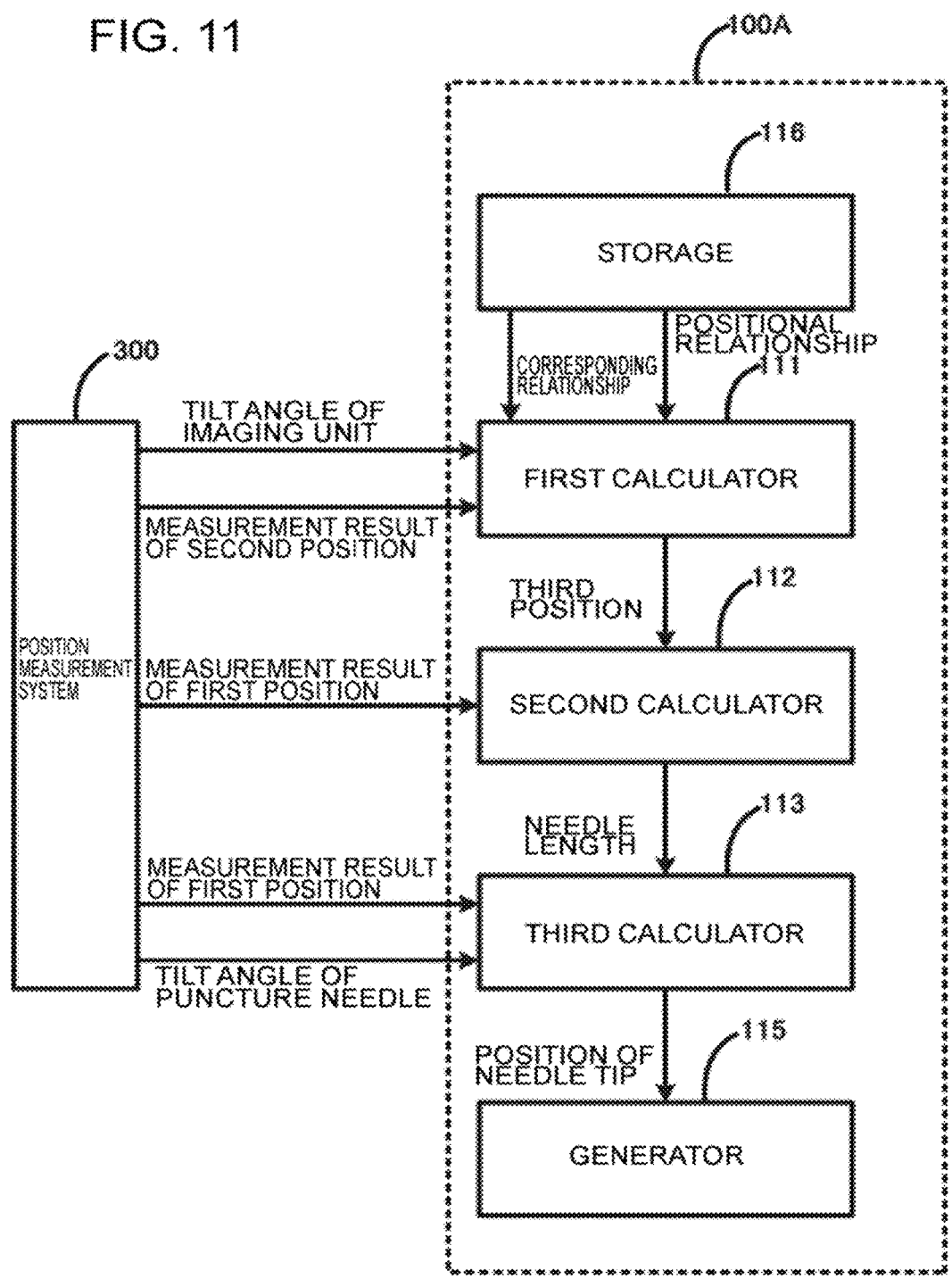
FIG. 11 is a block diagram of a guide information generator.

Next, the needle length information acquisition unit 100A is described with reference to FIG. 11. FIG. 11 is a block diagram illustrating the configuration of a guide information generator.

As illustrated in FIG. 11, the needle length information acquisition unit 100A includes a first calculator 111, a second calculator 112, a third calculator 113, a generator 115, and the storage 116. The needle length information acquisition unit 100A instructs the position measurement system 300 to perform measurements, and acquires measurement values (the XYZ coordinates of the first position, the tilt angles of the puncture needle, the XYZ coordinates of the second position, the tilt angles of the ultrasound probe 11) therefrom.

(Storage 116)

The storage 116 stores the positional relationship of the third position with respect to the second position. Here, the positional relationship includes the tilt angles (α, β, γ) of a straight line that connects the second position and the third position, and the length $R_1$ of the straight line. Here, α, β, γ are the tilt angles of the straight line with respect to the U-axis, the V-axis and the W-axis in the UVW coordinate system.

(First Calculator 111)

Described below is an example of the first calculator 111. The first calculator 111 obtains the XYZ coordinates ($x_3$, $y_3$, $z_3$) of the third position by substituting the XYZ coordinates ($x_2$, $y_2$, $z_2$) of the second position where the magnetic sensor 320 is arranged, the tilt angles (α, β, γ) of the straight line that connects the second position and the third position, and the length $R_1$ of the straight line in the following equation (1):

[Equation 1]

$$\begin{bmatrix} x_3 \\ y_3 \\ z_3 \end{bmatrix} = \begin{bmatrix} 1 & 0 & 0 \\ 0 & \cos\theta & -\sin\theta \\ 0 & \sin\theta & \cos\theta \end{bmatrix} \begin{bmatrix} \cos\delta & 0 & -\sin\delta \\ 0 & 1 & 0 \\ \sin\delta & 0 & \cos\delta \end{bmatrix} \begin{bmatrix} \cos\phi & -\sin\phi & 0 \\ \sin\phi & \cos\phi & 0 \\ 0 & 0 & 1 \end{bmatrix} \begin{bmatrix} R_1\cos\alpha \\ R_1\cos\beta \\ R_1\cos\gamma \end{bmatrix} + \begin{bmatrix} x_2 \\ y_2 \\ z_2 \end{bmatrix} \quad (1)$$

where, θ, δ and φ are rotation angles (tilt angles of the imaging unit) of the UVW coordinates when rotated about the U-axis, the V-axis and the W-axis to match the UVW coordinates with the XYZ coordinates.

(Second Calculator 112)

Described below is an example of the second calculator 112. The second calculator 112 obtains the needle length L, which is the distance from the tip of the puncture needle to the second measurement object by substituting the three-dimensional coordinates ($x_3$, $y_3$, $z_3$) of the third position obtained, and the three-dimensional coordinates ($x_1$, $y_1$, $z_1$) of the first position measured in the following equation (2):

[Equation 2]

$$L = ((x_3 - x_1)^2 + (y_3 - y_1)^2 + (z_3 - z_1)^2)^{1/2} \quad (2)$$

As described above, the position measurement system 300 is performs measurement when the needle tip comes in contact with the third position. The needle length L is determined based on the measured results.

(Third Calculator 113)

Described below is an example of the third calculator 113. For puncture, the needle tip is removed from the third position, and is inserted into the subject. During the puncture, the position measurement system 300 measures the XYZ coordinates of the first position and the tilt angles of the puncture needle.

The third calculator 113 obtains the position ($x_4$, $y_4$, $z_4$) of the needle tip by substituting the XYZ coordinates ($x_{11}$, $y_{11}$, $z_{11}$) of the first position, the tilt angles λ, μ, ω of the puncture needle with respect to the X-axis, the Y-axis, and the Z-axis, and the needle length L in the following equation (3):

[Equation 3]

$$\begin{bmatrix} x_4 \\ y_4 \\ z_4 \end{bmatrix} = \begin{bmatrix} L\cos\lambda \\ L\cos\mu \\ L\cos\omega \end{bmatrix} + \begin{bmatrix} x_{11} \\ y_{11} \\ z_{11} \end{bmatrix} \quad (3)$$

(Generator 115)

The needle length information acquisition unit 100A includes a generator 115. The generator 115 has software for drawing. By activating the software, the generator 115 generates guide information for guiding the needle tip by using the XYZ coordinates of the first position, the tilt angles of the puncture needle, the needle length, and the position of the needle tip obtained with a function expressed by the above equation (3) as parameters. The guide information includes an image of the position of the needle tip and an image of the ablation target range.

(Parameters)

Described next is the parameters used to generate the guide information. The parameters are stored in the storage 116 in advance in association with the type of the puncture needle.

The parameters indicate the specifications of the puncture needle and include the ablation target range, the color depth of the needle guideline, and display/non-display of the needle guideline.

Hereinafter the type of the puncture needle may be sometimes simply referred to as "needle type". The needle type is a concept including the type of the form of the puncture needle, the type of function of the puncture needle, the type of examination that uses the puncture needle (including purposes of the examination and a site to be examined). Examples of the needle type include the monopolar type in which one electrode is provided at the position of the tip of the puncture needle, and the bipolar type in which two electrodes are provided in a site at a predetermined distance from the tip of the puncture needle with an insulating part between them.

The "ablation target range" includes the shape, the size and the center position of the ablation target range. The "shape", "size" and the "center position" of the ablation target range vary depending on the type of the puncture needle (needle type). In the monopolar type, the "shape" is a circle, while in the bipolar type, it is elliptical. Besides, the "size" of the bipolar type is the radius of the circle, while that of the monopolar type is the length of the long axis of the ellipse.

In the monopolar type, the "center position" is the position of the tip of the puncture needle (position where an electrode is located). The position of the tip of the puncture needle is determined by the third calculator 113 as described above.

In the bipolar type, the "center position" is a position at a predetermined distance from the tip of the puncture needle (position where insulation is located). In addition, the position at the predetermined distance from the needle tip is obtained by a fourth calculator (not illustrated).

In the following, the shape, the size and the center position of the ablation target range are described assuming that the puncture needle is of the monopolar type. That is, the "shape" is a circle, and the "center position" is the position of the tip of the puncture needle.

The "color depth of the needle guideline" is used to thinly display the guideline when an image displayed below the guideline is not easily viewable.

The "display/non-display of the needle guideline" is used to display or not to display the guideline depending on whether an image displayed below the guideline is easily viewable.

Having received the position of the needle tip obtained by the third calculator 113, and the shape, the size and the center position of the ablation target range as the parameters stored in advance in the storage 116, the generator 115 generates a circle (ablation target range), centered at the position of the needle tip, with a predetermined radius as the guide information.

The generator 115 generates a needle guideline as the guide information based on the position of the tip of the puncture needle obtained by the third calculator 113 and the first position (where the magnetic sensor 310 is located) of the puncture needle measured by the position measurement system.

Having received the "color depth of the needle guideline" and the "display/non-display of the needle guideline" stored in advance as parameters in the storage 116, and the guide information (here, the needle guideline) generated by the generator 115, the display processor 118 displays or does not display a needle guideline NL on the display 21 such that it is superimposed on an echo image EG captured by the imaging unit. This enables the puncture needle to be accurately and easily inserted into the target site.

Figure 12:
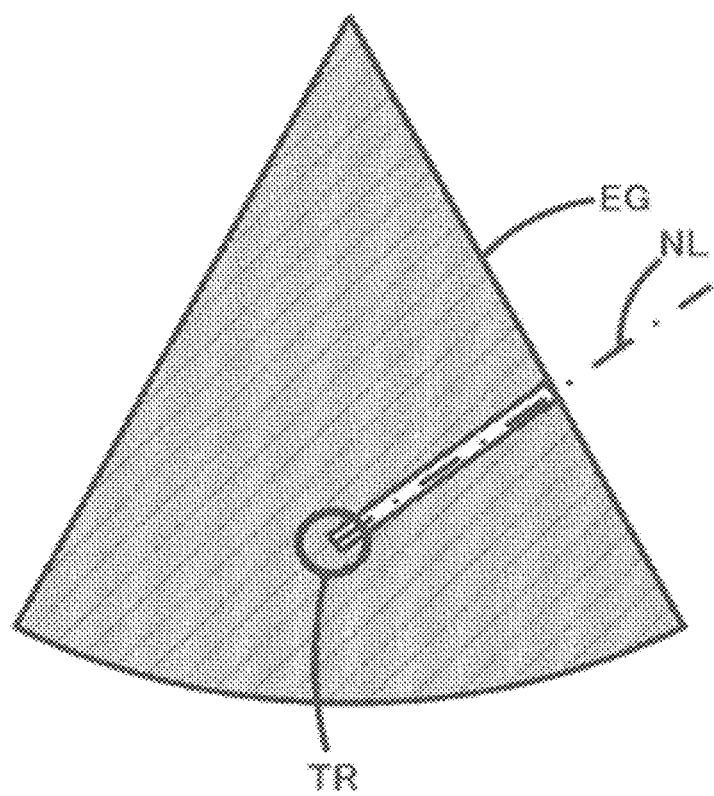
FIG. 12 is an example of guide information displayed as being superimposed on an echo image.

During the puncture, the position measurement system 300 measures the XYZ coordinates (x11, y11, z11) of the first position and the tilt angles ($\lambda$, $\mu$, $\omega$) of the puncture needle. During the puncture, the software for drawing of the generator 115 is run continuously, and an image of the position of the needle tip and an image of the ablation target range are generated by using the XYZ coordinates (x11, y11, z11) of the first position, the tilt angles ($\lambda$, $\mu$, $\omega$) of the puncture needle, the needle length L, and the position of the needle tip obtained with a function expressed by the above equation (3). In parallel with this, the echo image EG is captured by the imaging unit. FIG. 12 is a view illustrating the guide information displayed over the echo image EG. In FIG. 12, an image of the needle type that is rendered in the echo image EG is represented by a white portion, and the needle guideline NL displayed overlapped on the echo image EG is indicated by an alternate long and short dash line.

As illustrated in FIG. 12, the display processor 118 matches the coordinates of the ablation target range generated by the generator 115 with the coordinates at which the echo image EG is displayed. The display processor 118 then displays the ablation target range superimposed on the echo image EG on the display 21. The display of the ablation target range facilitates to match the ablation target range with the target site. FIG. 12 illustrates an ablation target range TR which is displayed as being superimposed on the echo image EG.

[Operation]

Figure 13:
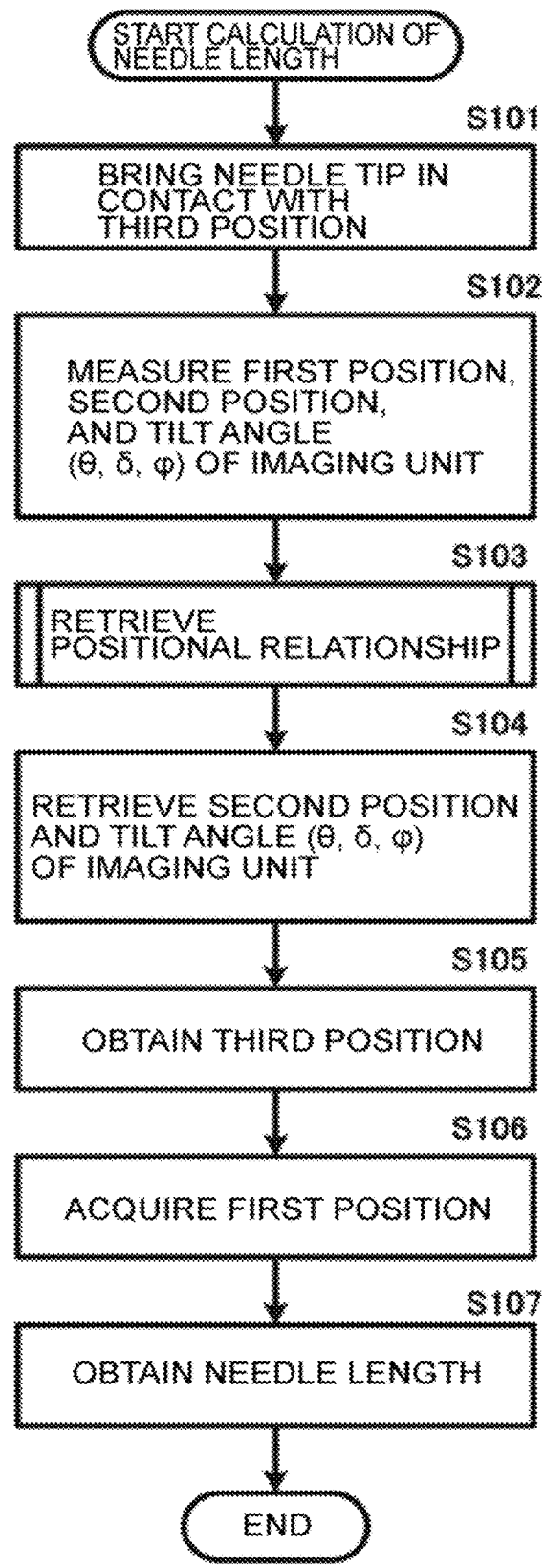
FIG. 13 is a flowchart illustrating a series of processes for calculating a needle length.

Next, the operation of the ultrasound diagnosis apparatus is described with reference to FIGS. 13 and 14. FIG. 13 is a flowchart illustrating a series of processes for calculating the needle length.

As illustrated in FIG. 13, first, the needle tip is brought in contact with the third position (step S101). At this time, the operator can easily bring the needle tip into contact with the third position just by bringing them close to each other while having the ultrasound probe 11 with one hand and the puncture needle with the other. Then, the position measurement system 300 measures the first position, the second position, and the tilt angle of the ultrasound probe 11 (imaging unit) (step S102).

The first position, the second position, and the tilt angle of the ultrasound probe 11 may be measured regardless of the order. After the measurement, the needle tip may be removed away from the third position, and also the tilt angle of the ultrasound probe 11 may be changed.

The first calculator 111 retrieves the positional relationship of the third position with respect to the second position and from the storage 116 (step S103). The first calculator 111 also retrieves the second position and the tilt angle of the ultrasound probe 11 (step S104).

Then, the first calculator 111 obtains the third position by substituting the positional relationship of the third position with respect to the second position, the second position, and the tilt angle of the ultrasound probe 11 in equation (1) (step S105).

Next, the second calculator 112 acquires the first position (step S106). The second calculator 112 then obtains the needle length by substituting the second position and the third position in equation (2) (step S107).

In the preliminary measurement for obtaining the needle length, the needle tip is brought into contact with the third position, and the position measurement system 300 measures the first position, the second position, and the tilt angle of the ultrasound probe 11. Thus, the needle length is determined based on the measurement result. In the measurement after the preliminary measurement, the needle tip is removed from the third position. In this measurement, the position measurement system 300 measures the first position and the tilt angle of the puncture needle, and the position of the needle tip is determined based on the measurement result. The generator 115 generates needle tip guide information, and the display 21 displays the needle tip guide information.

Next, with reference to FIG. 14, a description is given of the operation from processes from the calculation of the needle length until the display of the needle tip guide information superimposed on a medical image (echo image). FIG. 14 is a flowchart illustrating a series of processes from the calculation of the needle length until the display of the needle tip guide information. As illustrated in FIG. 14, the needle length is calculated (step S301), and thereafter, the position measurement system 300 measures the XYZ coordinates of the first position, and the tilt angle of the puncture needle (step S302).

The third calculator 113 then obtains the position of the needle tip by substituting the needle length, the XYZ coordinates of the first position, and the tilt angle of the puncture needle in equation (3) (step S303). After that, the generator 115 generates a needle guideline as the needle tip guide information based on the position of the needle tip and the XYZ coordinates of the first position (step S304). At this time, the ablation target range (including the center position, shape, and size) is generated as the needle tip guide information.

The display processor 118 converts the coordinates of the ablation target range into the coordinates at which the echo image EG is displayed (step S305). Then, the display processor 118 displays the ablation target range superimposed on the echo image EG on the display 21 (step S306).

Fourth Embodiment

Next, a description is given of a medical image diagnosis apparatus according to a fourth embodiment with reference to FIGS. 1 and 15 to 21. In the fourth embodiment, like reference numerals designate corresponding parts and the same description is not repeated. Differences are mainly described.

In the third embodiment, since the second position is provided relative to the third position, and the third position has one positional relationship with respect to the second position. In the case of a single third position, the needle tip is required to be constantly in contact with the third position while the needle length is obtained. However, depending on the location of the third position, it may be difficult to bring the needle tip in contact therewith. For this reason, a plurality of third positions is provided to remove such a difficulty in bringing the needle tip in contact by selecting one of them, with which the needle tip can be easily brought into contact.

In the fourth embodiment, a plurality of third position are provided with respect to the second position. The third positions have a plurality of positional relationships with respect to the second position. In other words, the first calculator 111 cannot obtain the third position based on the positional relationship unless one of the positional relationships is specified.

Figure 16:
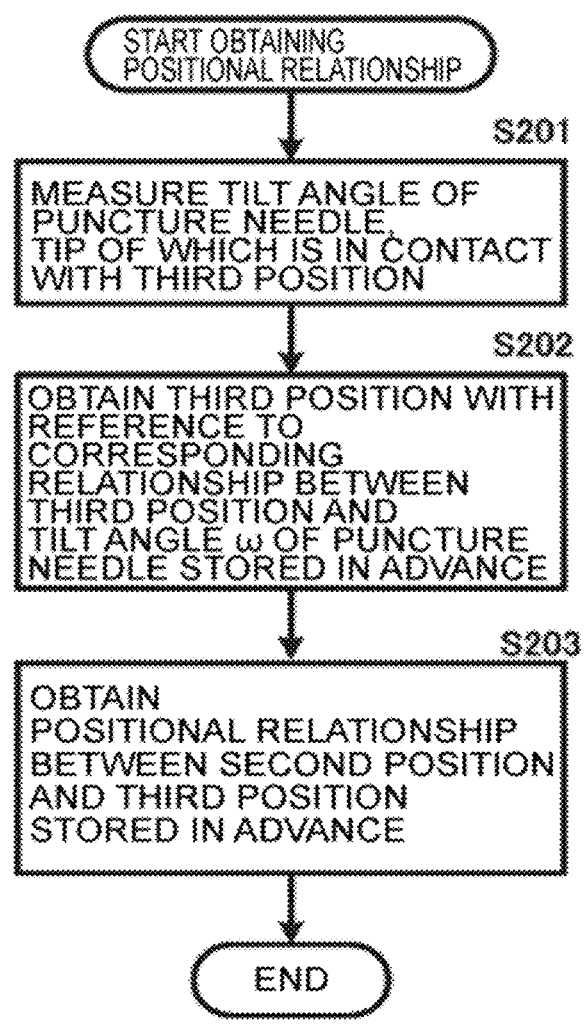
FIG. 16 is a flowchart illustrating a series of processes for obtaining a positional relationship between a second position and the third position.
Figure 17:
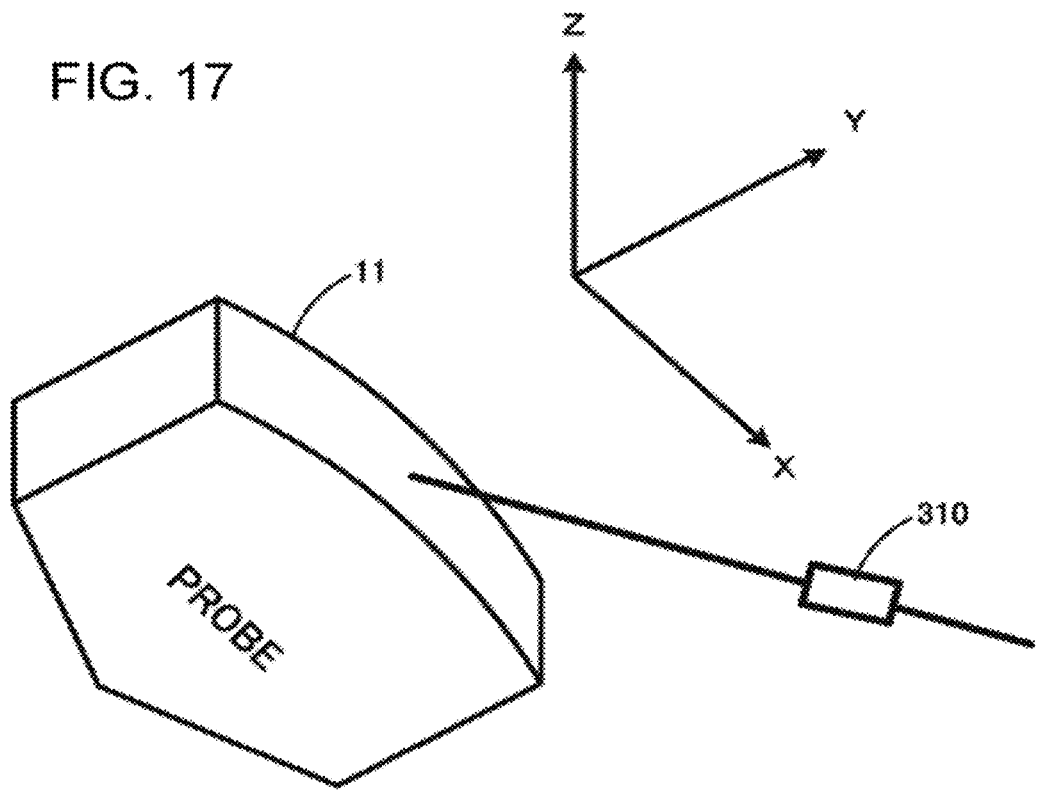
FIG. 17 is a diagram illustrating an example of the puncture needle, the tip of which is in contact with the third position.
Figure 18:
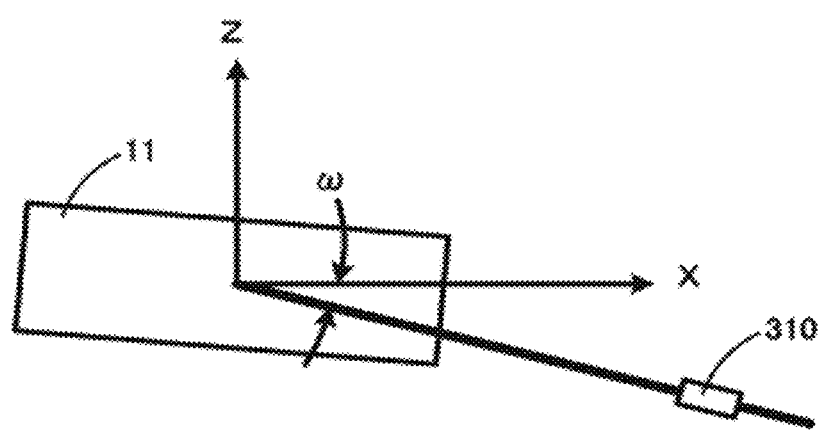
FIG. 18 is a diagram illustrating an example of the tilt angle of the puncture needle, the tip of which is in contact with the third position.
Figures 19, 20:
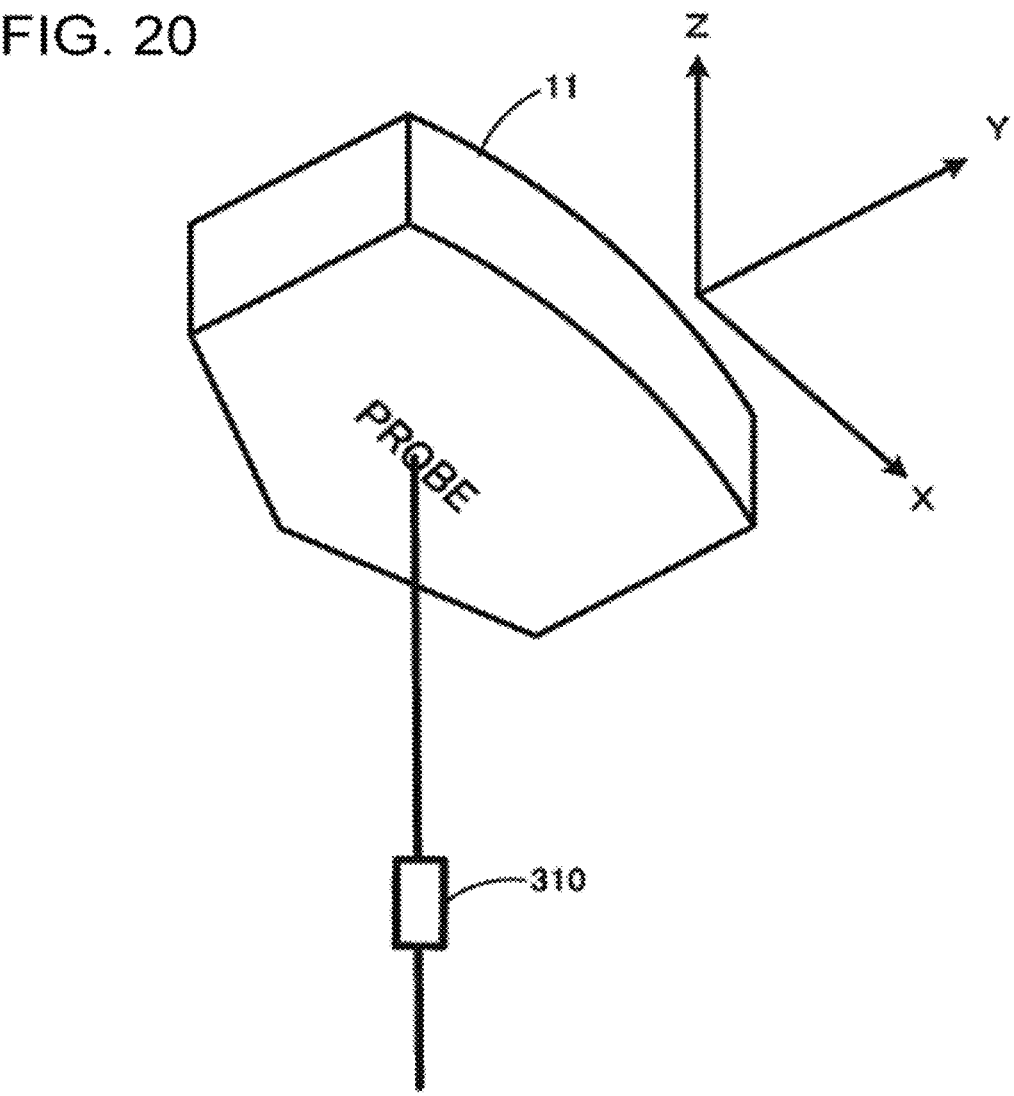
FIG. 19 is a diagram illustrating a positional relationship between the third position and the second position.
FIG. 20 is a diagram illustrating another example of the puncture needle, the tip of which is in contact with the third position.

In the fourth embodiment, an example is described in which one positional relationship is specified from a plurality of positional relationships with reference to FIGS. 15 to 19. FIG. 15 is a diagram illustrating the corresponding relationship between the tilt angle of the puncture needle and the third position. FIG. 16 is a flowchart illustrating a series of processes for obtaining the positional relationship between the second position and the third position. FIG. 17 is a diagram illustrating an example of the puncture needle, the tip of which is in contact with the third position. FIG. 18 is a diagram illustrating an example of the tilt angle of the puncture needle, the tip of which is in contact with the third position. FIG. 19 is a diagram illustrating the positional relationship between the third position and the second position.

The storage 116 stores the corresponding relationship between the tilt angle of the puncture needle and the third position in advance. As illustrated in FIG. 16, the position measurement system 300 measures the tilt angle of the puncture needle, the tip of which is in contact with the third position (step S201).

As illustrated in FIGS. 17 and 18, when the needle tip is in contact with the third position, the position measurement system 300 measures the tilt angle ω of the puncture needle. When the tilt angle ω with respect to the XY plane is in a range of −15° to 15°, the first calculator 111 obtains the third position, which is the center of the acoustic radiation surface of the ultrasound probe 11, with reference to the corresponding relationship as illustrated in FIG. 15 (step S202).

Having obtained the third position, the first calculator 111 obtains the positional relationship between the second position and the third position as illustrated in FIG. 19 (step S203). Incidentally, α1, β1 and γ1 each represent the tilt angle of a straight line that connects the second position and the third position at this time, and R1 represents the length of the straight line.

Figure 21:
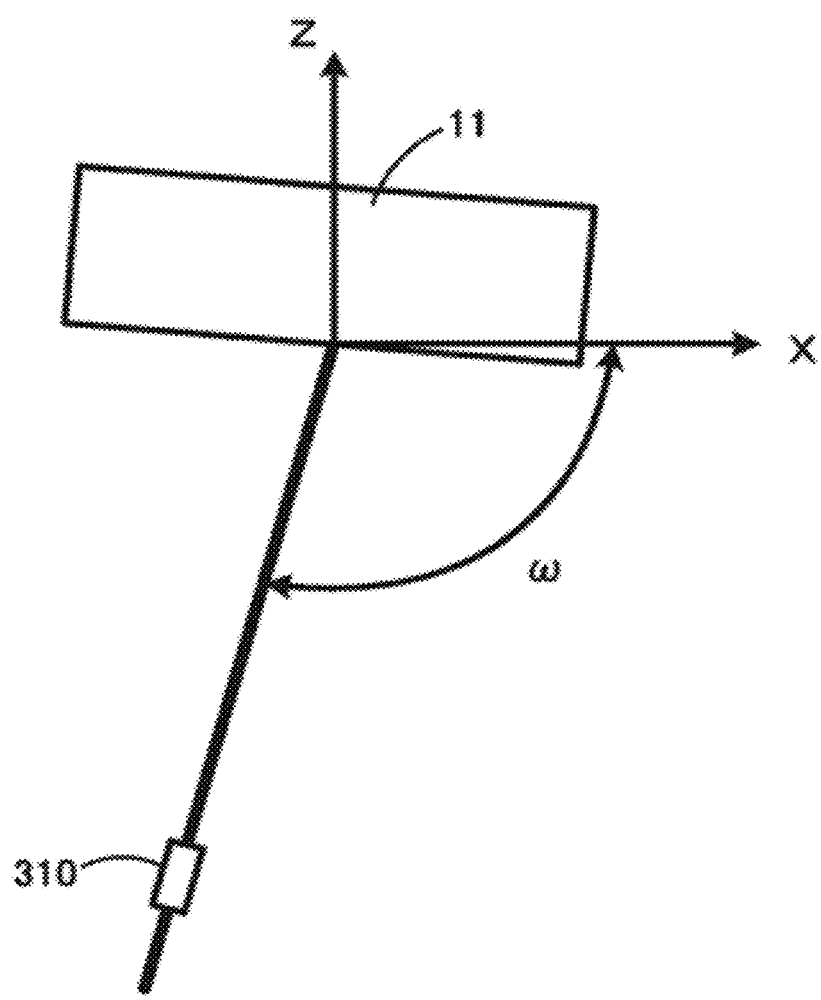
FIG. 21 is a diagram illustrating another example of the tilt angle of the puncture needle, the tip of which is in contact with the third position.

An example has been described of the positional relationship referenced to obtain the third position. Described below is another example of the positional relationship. FIG. 20 is a diagram illustrating another example of the puncture needle, the tip of which is in contact with the third position. FIG. 21 is a diagram illustrating another example of the tilt angle of the puncture needle, the tip of which is in contact with the third position.

As illustrated in FIGS. 20 and 21, when the needle tip is in contact with the third position, the position measurement system 300 measures the tilt angle co of the puncture needle. When the tilt angle ω with respect to the XY plane is in a range of 75° to 105° or −75° to 105°, the first calculator 111 obtains the third position, which is the position of the mark of the ultrasound probe 11, with reference to the corresponding relationship as illustrated in FIG. 15 (step S202).

Having obtained the third position, the first calculator 111 obtains the positional relationship between the second position and the third position as illustrated in FIG. 19 (step S203). Incidentally, α2, β2 and γ2 each represent the tilt angle of a straight line that connects the second position and the third position at this time, and R2 represents the length of the straight line.

In the above embodiments, the ultrasound diagnosis apparatus is described as an example of the medical image diagnosis apparatus, and the ultrasound probe 11 is described as an example of the imaging unit; however, it is not so limited. An X-ray CT apparatus may be cited as another example of the medical image diagnosis apparatus. As an example of the imaging unit of the X-ray CT apparatus, there is a bed apparatus on which a subject is placed. In this case, the bed apparatus is provided with the second position and the third position.

Besides, the position measurement system 300 is taken as an example of a means for measuring the first position arranged in the puncture needle and the second position arranged in the ultrasound probe 11; however, anything may be used as long as it is capable of measuring the three-dimensional coordinates of the first position and the second position as well as the tilt angle of the ultrasound probe 11.

Further, while an example is described in which the needle tip is brought in contact with the third position, it may be brought in contact with the second position. In this case, the third position corresponds to the second position.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
an ultrasound probe configured to transmit and receive ultrasound waves to and from a subject, the ultrasound probe including a first sensor;
a reference position member arranged on the ultrasound probe;
processing circuitry configured to
acquire position information of the first sensor and of a second sensor located in a position having a predetermined positional relationship to a puncture needle,
determine position information of the reference position member based on the acquired position information of the first sensor and a distance between the first sensor and the reference position member, and
determine a needle length indicating a length of the puncture needle, based on the position information of the reference position member and the second sensor at a time when a tip of the puncture needle is in contact with the reference position member; and
a display to display information to guide a puncture by the puncture needle based on the determined needle length.

2. The ultrasound diagnosis apparatus of claim 1, wherein
the reference position member is a sensitive element configured to react to the tip of the puncture needle when the tip approaches within a predetermined distance, and
the processing circuitry is further configured to acquire the needle length information in response to a reaction of the sensitive element to the tip of the puncture needle.

3. The ultrasound diagnosis apparatus of claim 2, further comprising:
a transmitter configured to transmit a reference signal to a three-dimensional space, wherein
the first sensor is arranged on a support of the ultrasound probe,
the second sensor is arranged on the puncture needle,
the first sensor and the second sensor are configured to receive the reference signal from the transmitter,
the processing circuitry is further configured to calculate the length from the second sensor to the tip of the puncture needle as the needle length, based on three-dimensional spatial position information of the first sensor and the second sensor in response to the reaction of the sensitive element, and
the display further displays a medical image including a navigation image for navigating the puncture, based on the calculated needle length.

4. The ultrasound diagnosis apparatus of claim 2, wherein the sensitive element is a conductor, through which a current flows from the puncture needle when in contact with the puncture needle.

5. The ultrasound diagnosis apparatus of claim 2, wherein the sensitive element is a pressure-sensitive sensor configured to detect a contact with the puncture needle.

6. The ultrasound diagnosis apparatus of claim 2, wherein the sensitive element is a proximity sensor or a camera configured to detect an approach of the puncture needle.

7. The ultrasound diagnosis apparatus of claim 1, wherein
the second sensor is located at a first position of the puncture needle,
the ultrasound probe is provided with a second position and a third position, the third position having a predetermined positional relationship with the second position, and
the processing circuitry is further configured to
measure three-dimensional coordinates of the first position, three-dimensional coordinates of the second position, and a tilt angle of the ultrasound probe, when the tip of the puncture needle is located at the third position, and
obtain the needle length corresponding to a distance from the first position to the tip of the puncture needle, based on the measured three-dimensional coordinates of the first and second positions and the predetermined positional relationship, and display guide information for guiding the puncture needle.

8. The ultrasound diagnosis apparatus of claim 7, wherein
the processing circuitry is further configured to
obtain three-dimensional coordinates of the third position based on the three-dimensional coordinates of the second position and the tilt angle of the ultrasound probe with reference to the predetermined positional relationship, and
determine the needle length based on the three-dimensional coordinates of the first position and the three-dimensional coordinates of the third position.

9. The ultrasound diagnosis apparatus of claim 8, wherein the tip of the puncture needle is located at the third position when brought in contact with the third position.

10. The ultrasound diagnosis apparatus of claim 8, wherein
the third position includes a plurality of third positions,
the ultrasound diagnosis apparatus further comprises a memory to store a corresponding relationship between each of the third positions and a tilt angle of the puncture needle in advance, and
the processing circuitry is further configured to
measure the tilt angle of the puncture needle when the tip of the puncture needle is aligned in the third position, and
detect one of the third positions in which the tip of the puncture needle is aligned based on the tilt angle of the puncture needle with reference to the corresponding relationship, and refer to a predetermined positional relationship between the second position and the one of the third positions to obtain the three-dimensional coordinates of the third position.

11. The ultrasound diagnosis apparatus of claim 7, wherein
the processing circuitry is further configured to
measure a tilt of the puncture needle after obtaining the needle length,
obtain a position of the tip of the puncture needle based on the needle length and the tilt of the puncture needle,
generate the guide information based on the position of the tip of the puncture needle, and
match coordinates of the guide information with coordinates at which a medical image captured by scanning a target site of the subject and the puncture needle inserted in the target site is displayed, and
the display further displays the guide information superimposed on the medical image.

12. A medical image diagnosis apparatus, comprising:
an imager configured to capture a medical image by scanning a target site of a subject, the imager including a first sensor;
a reference position member arranged on the imager;
processing circuitry configured to
   acquire position information of the first sensor and of a second sensor located in a position having a predetermined positional relationship to a puncture needle, and
   acquire position information of the reference position member based on the acquired position information of the first sensor and a distance between the first sensor and the reference position member, and
   determine a needle length indicating a length of the puncture needle, based on the position information of the reference position member and the second sensor, at a time when a tip of the puncture needle is in contact with the reference position member; and
a display to display information to guide a puncture by the puncture needle based on the acquired needle length.

* * * * *